US012715850B2

(12) United States Patent
Green et al.

(10) Patent No.: US 12,715,850 B2
(45) Date of Patent: Aug. 25, 2026

(54) LOW TOXICITY NMP SUBSTITUTES AND USES THEREOF

(71) Applicant: Advancion Corporation, Buffalo Grove, IL (US)

(72) Inventors: G. David Green, Cary, IL (US); Jordan Quinn, Mundelein, IL (US)

(73) Assignee: Advancion Corporation, Buffalo Grove, IL (US)

( * ) Notice: Subject to any disclaimer, the term of this patent is extended or adjusted under 35 U.S.C. 154(b) by 692 days.

(21) Appl. No.: 17/799,249

(22) PCT Filed: Feb. 11, 2021

(86) PCT No.: PCT/US2021/017686
§ 371 (c)(1),
(2) Date: Aug. 11, 2022

(87) PCT Pub. No.: WO2021/163348
PCT Pub. Date: Aug. 19, 2021

(65) Prior Publication Data

US 2023/0130822 A1 Apr. 27, 2023

Related U.S. Application Data

(60) Provisional application No. 62/976,469, filed on Feb. 14, 2020.

(51) Int. Cl.

| | |
|---|---|
| ***C07D 265/30*** | (2006.01) |
| ***C07C 229/12*** | (2006.01) |
| ***C07C 237/06*** | (2006.01) |
| ***C07D 207/267*** | (2006.01) |
| ***C07D 207/277*** | (2006.01) |
| ***C07D 207/40*** | (2006.01) |
| ***C07D 261/02*** | (2006.01) |
| ***C07D 263/22*** | (2006.01) |
| ***C07D 295/185*** | (2006.01) |

(52) U.S. Cl.
CPC .......... *C07D 265/30* (2013.01); *C07C 229/12* (2013.01); *C07C 237/06* (2013.01); *C07D 207/267* (2013.01); *C07D 207/277* (2013.01); *C07D 207/40* (2013.01); *C07D 261/02* (2013.01); *C07D 263/22* (2013.01); *C07D 295/185* (2013.01)

(58) Field of Classification Search
CPC . C07C 229/12; C07C 237/06; C07D 207/267; C07D 207/277; C07D 207/40; C07D 261/02; C07D 263/22; C07D 295/185
See application file for complete search history.

(56) References Cited

U.S. PATENT DOCUMENTS

| | | | |
|---|---|---|---|
| 4,865,758 | A | 9/1989 | Caster et al. |
| 2015/0057375 | A1 | 2/2015 | Vandeputte et al. |

FOREIGN PATENT DOCUMENTS

| | | | |
|---|---|---|---|
| EP | 0 293 816 | A2 | 12/1988 |
| EP | 0 755 987 | A1 | 1/1997 |
| GB | 1 326 222 | A | 8/1973 |

(Continued)

OTHER PUBLICATIONS

Davies; Journal of the American Chemical Society 2016, 138 (26), 8092-8095. Supporting Information, pp. S1-S247. (Year: 2016).*

(Continued)

*Primary Examiner* — Golam M Shameem
(74) *Attorney, Agent, or Firm* — Foley & Lardner LLP

(57) ABSTRACT

The present technology is directed to compounds Formulas I, II, III, and IV as well as compositions that include one or more of the compounds and methods of making the compounds. In particular, the present compounds may be used as a replacement for NMP in compositions to produce lower toxicity compositions.

Formula I

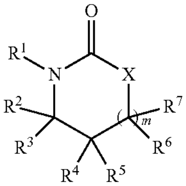

Formula II

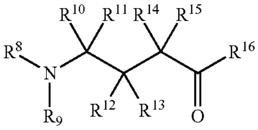

Formula III

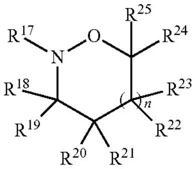

Formula IV

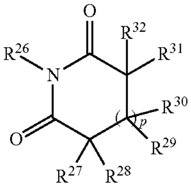

18 Claims, No Drawings

(56) References Cited

FOREIGN PATENT DOCUMENTS

| | | | | |
|---|---|---|---|---|
| JP | S46-032263 | A | 11/1971 | |
| JP | S57-130978 | A | 8/1982 | |
| JP | H01-289878 | A | 11/1989 | |
| JP | H04-095067 | A | 3/1992 | |
| JP | 2013-522296 | A | 6/2013 | |
| JP | 2015-237411 | A | 6/2017 | |
| WO | WO-2005/090430 | A1 | 9/2005 | |
| WO | WO-2005/090447 | A2 | 9/2005 | |
| WO | WO-2008012231 | A2 * | 1/2008 | ......... C07D 207/267 |
| WO | WO-2013/107822 | A1 | 7/2012 | |

OTHER PUBLICATIONS

Communication pursuant to Rule 161(1) and 162 EPC in EP 21709859.9 DTD Sep. 21, 2022, 4 pages.
Davies, et al., "Visible-Light-Mediated Synthesis of Amidyl Radicals: Transition-Metal-Free Hydroamination and N-Arylation Reactions", Journal of The American Chemical Society, vol. 138, No. 26, 2016, pp. 8092-8095.
Dolby, et al., "The total synthesis of (±)-dasycarpidone and (±)-epidasycarpidone", Journal of the American Chemical Society, vol. 90, No. 10, 1968, pp. 2699-2700.
Fournier, et al., "Imidazolium and Potassium Hydrogen Carbonate Salts as Ecofriendly Organocatalysts for Oxazolidinone Synthesis", European Journal of Organic Chemistry, vol. 2016, No. 21, 2016, pp. 3514-3518.
Imada, et al., "Palladium-Catalyzed Double and Single Carbonylations of β-Amino Alcohols. Selective Synthesis of Morpholine-2, 3-diones and Oxazolidin-2-Ones and Applications for Synthesis of α-Oxo Carboxylic Acids", Bulletin of the Chemical Society of Japan, vol. 69, No. 7, 1996, pp. 2079-2090.
International Preliminary Report on Patentability on PCT/US2021/017686 on Aug. 25, 2022, 17 pages.
International Search Report / Written Opinion on PCT PCT/US2021/017686 DTD Oct. 8, 2021, 25 pages.
Invitation to Pay Additional Fees and, Where Applicable, Protest Fee issued in PCT/US2021/017686 DTD Aug. 4, 2021, 10 pages.
Juarez, et al., "Ceria nanoparticles as heterogeneous catalyst for $CO_2$ fixation by ω-aminoalcohols", Chemical Communications, vol. 46, No. 23, 2010, pp. 4181-4183.
Kametani, et al., "A Synthesis of 4-Oxa-9-aza-9-methyl-6, 7-benzobicyclo [3. 3. 1] nonane and attempts to Cyclize the Piperidone Derivatives by Reductive Cyclization: Studies on the Syntheses of Heterocyclic Compounds. CCXXVII", The Pharmaceutical Society of Japan, vol. 88, No. 5, 1968, pp. 573-582.
Murdock, K. C., "2-Oxazolidinones from an N-Dealkylation reaction of phosgene with dialkylaminoalkanols. The isolation and reactivities of an N-acyl quaternary ammonium intermediate", Journal of Organic Chemistry, vol. 33, No. 4, 1968, pp. 1367-1371.
Nakagawa, et al., "Regio- and Enantioselective Intramolecular Amide Carbene Insertion into Primary C—H Bonds Using Ru (II)-Pheox Catalyst", Journal of Organic Chemistry, vol. 84, No. 5, 2019, pp. 2607-2618.
Nguyen, et al., "PCET-Enabled Olefin Hydroamidation Reactions with N-Alkyl Amides", vol. 9, No. 5, 2019, pp. 4502-4507.
Rajanbabu, T. V., "Dibutyltin Oxide" In: "Encyclopedia of reagents for organic synthesis; vol. 7, Sod-Trim", Wiley, 2001, pp. 1-3.
Yadav, et al., "Novelty of immobilized enzymatic synthesis of 3-ethyl-1,3-oxazolidin-2-one using 2-aminoalcohol and dimethyl carbonate: Mechanism and kinetic modeling of consecutive reactions", Journal of Molecular Catalysis B: Enzymatic, vol. 109, 2014, pp. 62-69.
Bryantsev et al., "Predicting Autoxidation Stability of Ether- and Amide-Based Electrolyte Solvents for Li-Air Batteries", The Journal of Physical Chemistry, 2012, vol. 116, pp. 7128-7138.
Davies et al., "Visible-Light-Mediated Synthesis of Amidyl Radicals: Transition-Metal=Free Hydroamination and N-Arylation Reactions", Journal Of The American Chemical Society, 2016, vol. 138, pp. 8092-8095.
K.C. Murdock, "2-Oxazolidinones from an N-Dealkylation Reaction of Phosgene with Dialkylaminoalkanols. The Isolation and Reactivities of an N-Acyl Quaternary Ammonium Intermediate", The Journal of Organic Chemistry, 1968, vol. 33, No. 4, pp. 1367-1371.
Office Action on CN 202180023512.8 DTD Dec. 5, 2024, 13 pages including English translation.
Office Action on JP 2022-548575 DTD Dec. 16, 2024, 19 pages including English translation.
Tominaga et al., "Synthesis of 2-Oxazolidinones from CO2 and 1,2-Aminoalcohols Catalyzed by n-Bu2SnO", Synlett, 2002, No. 2, pp. 307-309.
Decision of Refusal and Written Opinion on JP 2022-548575 DTD Sep. 4, 2025, 66 pages including English machine translation.
Notice of Preliminary Rejection on KR 2022-7030861 DTD Jul. 21, 2025, 24 pages including English translation.
Second Office Action CN 2021800235128 DTD Jun. 18, 2025, 11 pages including English translation.
Decision of Rejection on CN 2021800235128 DTD Nov. 28, 2025, 14 pages (including English translation).
Pre-Appeal Examination Report on JP 2022-548575 dated Apr. 27, 2026, 10 pages including English translation.
The Chemical Society of Japan, Handbook of Chemistry: Applied Chemistry, 5th edition, Maruzen Co., Ltd., 1995, pp. I-443 and I-444 (including partial translation).
The Chemical Society of Japan, Handbook of Chemistry: Applied Chemistry, 6th edition, Maruzen Co., Ltd., 2003, pp. 788, 789, 1007, 1050 (including partial translation).
The Chemical Society of Japan, Handbook of Chemistry: Applied Chemistry, 7th edition, Maruzen Co., Ltd., 2014, pp. 958-963 (including partial translation).

* cited by examiner

LOW TOXICITY NMP SUBSTITUTES AND USES THEREOF

CROSS REFERENCE TO RELATED APPLICATION

This application is a U.S. National Phase Application under 35 U.S.C. § 371 of International Application No. PCT/US2021/017686, filed Feb. 11, 2021, which claims priority to U.S. Provisional Patent Application No. 62/976,469, filed on Feb. 14, 2020, the entire contents of which are incorporated herein by reference in their entireties.

BACKGROUND

The present technology relates generally to the field of N-methylpyrrolidone (NMP) substitutes. NMP also known as N-methyl-2-pyrrolidone or 1-methyl-2-pyrrolidinone is a colorless to slightly yellow liquid with a slight amine or "fishy" odor. NMP is used in wide variety of applications such as in paints or coatings, strippers, cleaners, adhesives/binders/sealants, leather treatment, personal care compositions, screen printing, pharmaceutical formulations, and manufacturing.

NMP is well absorbed following inhalation, oral and dermal exposure in humans and animals. In experimental animals, NMP had low toxicity following exposure to high levels over short time by inhalation, dermal exposure, and ingestion, however, when animals ingested NMP repeatedly at lower levels, adverse effects included changes in body weight, liver weight, neurotoxicity, and thymus atrophy. Long-term oral exposures in animals also caused increased incidence of large kidneys, kidneys diagnosed with chronic problems, fluid in the pleural cavity and small testes. In an oral reproduction toxicity study, NMP caused developmental toxicity such as a decrease in fetal weight and malformations. These effects were noted at doses lower than those that caused maternal toxicity, indicating that maternal toxicity did not cause the developmental toxicity. Additional information on toxicity and health effect of NMP can be found at U.S. Environmental Protection Agency, 2015, "TSCA Work Plan Chemical Risk Assessment. N-Methylpyrrolidone: Paint Stripper Use"; U.S. Environmental Protection Agency, 2017, "Scope of the Risk Evaluation for N-Methylpyrrolidone (2-Pyrrolidinone, 1-Methyl-)," Office of Chemical Safety and Pollution Prevention, EPA Document #EPA-740-R1-7005; S. Environmental Protection Agency, 2018, "Problem Formulation of the Risk Evaluation for N-Methylpyrrolidone (2-Pyrrolidinone, 1-Methyl-)," Office of Chemical Safety and Pollution Prevention, EPA Document #EPA-740-R1-7015; Organisation for Economic Co-operation and Development, 2007, "SIDS Initial Assessment Report on 1-Methyl-2-pyrrolidone. Organization for Economic Cooperation and Development;" National Institute for Public Health and the Environment (Netherlands), 2013, "Annex XV Restriction Report: Proposal for a Restriction. In RIVM, Bureau REACH," Version 2, The Netherlands: National Institute for Public Health and the Environment (RIVM), each of which is incorporated by reference.

In view of toxicity associated with NMP, a substitute for NMP is needed.

SUMMARY OF THE INVENTION

In one aspect, the present technology provides a compound of Formula I, Formula II, Formula III, or Formula IV:

Formula I

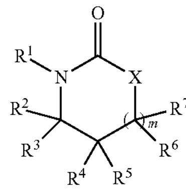

Formula II

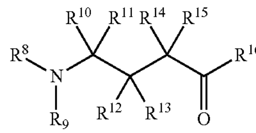

Formula III

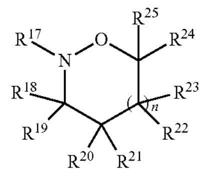

Formula IV

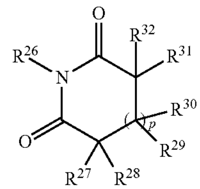

wherein: X may be O or $CR^{33}R^{34}$; $R^1$, $R^8$, $R^9$, $R^{17}$, and $R^{26}$ may each independently be —$CH_3$, —$CH_2CH_3$, —$CH_2CH_2CH_3$, or —$CH(CH_3)_2$; $R^2$, $R^3$, $R^{10}$, $R^{11}$, $R^{14}$, and $R^{15}$ may each independently be —H, —$CH_3$, or —$CH_2CH_3$; $R^6$ and $R^7$ may each independently be absent, —H, —$CH_3$, —$CH_2CH_3$, —CN, —$C(O)N(CH_3)_2$, —$CH_2C(O)N(CH_3)_2$, —$C(O)N(CH_2CH_3)_2$, —$CH_2C(O)N(CH_2CH_3)_2$, —$CO_2CH_3$, or —$CH_2CO_2CH_3$; $R^{16}$ may be —O—$C_1$-$C_8$ alkyl, —O—$C_2$-$C_8$ (hetero)cycloalkyl, —O—$C_4$-$C_{12}$ (hetero)aryl, —$NH_2$, —NH—$C_1$-$C_8$ alkyl, —N($C_1$-$C_8$ alkyl)$_2$,

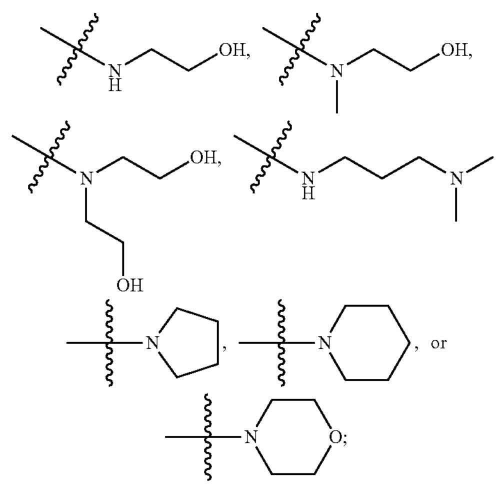

, or

;

$R^{18}$ and $R^{19}$ may each independently be —H or —$C_1$-$C_8$ alkyl; $R^{22}$ and $R^{23}$ may each independently be absent, —H or —$C_1$-$C_8$ alkyl; $R^{24}$ and $R^{25}$ may each independently be —H, —CN, —$C_1$-$C_8$ alkyl, —$C_2$-$C_8$ (hetero)cycloalkyl, —$CH_2$—O—$C_1$-$C_8$ alkyl, —C(O)—$C_1$-$C_8$ alkyl, —$C_1$-$C_8$ alkylene-C(O)—$C_1$-$C_8$ alkyl, —C(O)—$C_2$-$C_8$ (hetero)cycloalkyl, —$C_1$-$C_8$ alkylene-C(O)—$C_2$-$C_8$ (hetero)cycloalkyl, —$CO_2$H, —$CO_2$—$C_1$-$C_8$ alkyl, —$C_1$-$C_8$ alkylene-$CO_2$—$C_1$-$C_8$ alkyl, —$CO_2$—$C_2$-$C_8$ (hetero)cycloalkyl, —$C_1$-$C_8$ alkylene-$CO_2$—$C_2$-$C_8$ (hetero)cycloalkyl, —$C_1$-$C_8$ alkylene-$NH_2$, —$C_1$-$C_8$ alkylene-NH—$C_1$-$C_8$ alkyl, —$C_1$-$C_8$ alkylene-N($C_1$-$C_8$ alkyl$)_2$, —C(O)$NH_2$, —$C_1$-$C_8$ alkylene-C(O)$NH_2$, —C(O)NH—$C_1$-$C_8$ alkyl, —C(O)N($C_1$-$C_8$ alkyl$)_2$, —$C_1$-$C_8$ alkylene-C(O)NH—$C_1$-$C_8$ alkyl, —$C_1$-$C_8$ alkylene-C(O)N($C_1$-$C_8$ alkyl$)_2$, -(hetero)aryl, -(hetero)cycloalkyl,

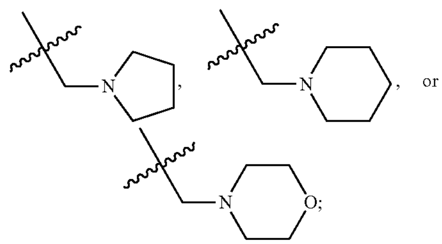

$R^4$, $R^5$, $R^{12}$, $R^{13}$, $R^{20}$, $R^{21}$, $R^{31}$, $R^{32}$, $R^{33}$, and $R^{34}$ may each independently be —H, —CN, —$C_1$-$C_8$ alkyl, —$C_2$-$C_8$ (hetero)cycloalkyl, —O—$C_1$-$C_8$ alkyl, —$CH_2$—O—$C_1$-$C_8$ alkyl, —C(O)—$C_1$-$C_8$ alkyl, —$C_1$-$C_8$ alkylene-C(O)—$C_1$-$C_8$ alkyl, —C(O)—$C_3$-$C_8$ cycloalkyl, —$C_1$-$C_8$ alkylene-C(O)—$C_2$-$C_8$ (hetero)cycloalkyl, —$CO_2$H, —$CO_2$—$C_1$-$C_8$ alkyl, —$C_1$-$C_8$ alkylene-$CO_2$—$C_1$-$C_8$ alkyl, —$CO_2$—$C_2$-$C_8$ (hetero)cycloalkyl, —$C_1$-$C_8$ alkylene-$CO_2$—$C_2$-$C_8$ (hetero) cycloalkyl, —$NH_2$, —$C_1$-$C_8$ alkylene-$NH_2$, —NH—$C_1$-$C_8$ alkyl, —N($C_1$-$C_8$ alkyl$)_2$, —$C_1$-$C_8$ alkylene-NH—$C_1$-$C_8$ alkyl, —$C_1$-$C_8$ alkylene-N($C_1$-$C_8$ alkyl$)_2$, —C(O)$NH_2$, —$C_1$-$C_8$ alkylene-C(O)$NH_2$, —C(O)NH—$C_1$-$C_8$ alkyl, —C(O)N($C_1$-$C_8$ alkyl$)_2$, —$C_1$-$C_8$ alkylene-C(O)NH—$C_1$-$C_8$ alkyl, —$C_1$-$C_8$ alkylene-C(O)N($C_1$-$C_8$ alkyl$)_2$, -(hetero) aryl, -(hetero)cycloalkyl,

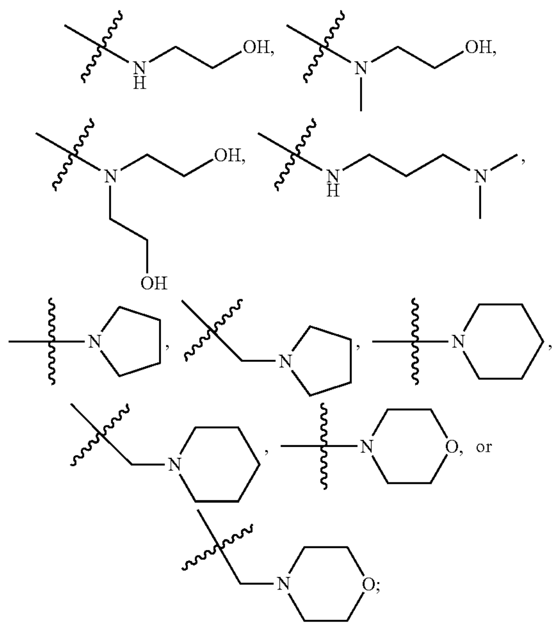

$R^{27}$ and $R^{28}$ may each independently be —H or —Z—$NR^{35}R^{36}$, wherein: Z may be a $C_1$-$C_8$ alkyl; and $R^{35}$ and $R^{36}$ may each independently be —H, —$C_1$-$C_8$ alkyl, -(hetero)aryl, -(hetero)cycloalkyl, —$C_1$-$C_8$ alkylene-OH, —$C_1$-$C_8$ alkylene-$NH_2$, —$C_1$-$C_8$ alkylene-NH—$C_1$-$C_8$ alkyl, or —$C_1$-$C_8$ alkylene-N—($C_1$-$C_8$ alkyl$)_2$; $R^{29}$ and $R^{31}$ may each independently be absent, —H, —$CH_3$, or —$CH_2CH_3$; and m, n, and p may each independently be 0 or 1.

The present technology also provides a composition that may include a compound of Formula I, Formula II, Formula III, Formula IV, or a combination thereof. In any embodiment, the composition may be substantially free of NMP. In any embodiment, the compound may be used as a replacement (i.e., substitute) for NMP in the composition.

DETAILED DESCRIPTION

The following terms are used throughout as defined below.

As used herein and in the appended claims, singular articles such as "a" and "an" and "the" and similar referents in the context of describing the elements (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the embodiments and does not pose a limitation on the scope of the claims unless otherwise stated. No language in the specification should be construed as indicating any non-claimed element as essential.

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term.

In general, "substituted" refers to an organic group as defined below (e.g., an alkyl group) in which one or more bonds to a hydrogen atom contained therein are replaced by a bond to non-hydrogen or non-carbon atoms. Substituted groups also include groups in which one or more bonds to a carbon(s) or hydrogen(s) atom are replaced by one or more bonds, including double or triple bonds, to a heteroatom. Thus, a substituted group is substituted with one or more substituents, unless otherwise specified. In some embodiments, a substituted group is substituted with 1, 2, 3, 4, 5, or 6 substituents. Examples of substituent groups include: halogens (i.e., F, $C_1$, Br, and I); $CF_3$; hydroxyls; alkoxy, alkenoxy, aryloxy, aralkyloxy, heterocyclyl, heterocyclylalkyl, heterocyclyloxy, and heterocyclylalkoxy groups; carbonyls (oxo); carboxylates; esters; urethanes; oximes; hydroxylamines; alkoxyamines; aralkoxyamines; thiols; sulfides; sulfoxides; sulfones; sulfonyls; pentafluorosulfanyl (i.e., $SF_5$), sulfonamides; amines; N-oxides; hydrazines; hydrazides; hydrazones; azides; amides; amines; ureas; amidines; guanidines; enamines; imides; isocyanates; isothiocyanates; cyanates; thiocyanates; imines; nitro groups; nitriles (i.e., CN); and the like.

The term "leaving group" or "LG" refers to groups readily displaceable by a nucleophile, such as an amine, alcohol, phosphorus, or thiol nucleophile or their respective anions. Such leaving groups are well known and include carboxylates, N-hydroxysuccinimide, N-hydroxybenzotriazole, halogen (halides including $Cl^-$, $Br^-$, and $I^-$), triflates, tosylates, mesylates, alkoxy, thioalkoxy, phosphinates, phosphonates and the like. In addition, the term "leaving group" or "LG" is meant to encompass leaving group precursors (i.e., moieties that can easily be converted to a leaving group upon simply synthetic procedures such as alkylation, oxidation or protonation). Such leaving group precursors and methods for converting them to leaving groups are well known to those of ordinary skill in the art.

Substituted ring groups such as substituted cycloalkyl, aryl, heterocyclyl and heteroaryl groups also include rings and ring systems in which a bond to a hydrogen atom is replaced with a bond to a carbon atom. Therefore, substituted cycloalkyl, aryl, heterocyclyl and heteroaryl groups may also be substituted The term "alkyl" refers to a group, whether alone or as part of another group (e.g., in dialkylamino), encompasses straight and branched chain aliphatic groups (i.e., saturated hydrocarbyl chains), and, unless otherwise indicated, has 1-10, alternatively 1-8, or alternatively 1-6 alkyl carbon atoms. Preferred alkyl groups include, without limitation, methyl, ethyl, propyl, isopropyl, butyl, isobutyl, sec-butyl, tert-butyl, pentyl, and hexyl. Unless otherwise indicated, the alkyl group is optionally substituted with 1, 2, or 3, preferably 1 or 2, more preferably 1, substituents that are compatible with the compounds, monomers, and polymers described herein.

Representative substituted alkyl groups may be substituted one or more times with substituents such as those listed above, and include without limitation haloalkyl (e.g., trifluoromethyl), hydroxyalkyl, thioalkyl, aminoalkyl, alkylaminoalkyl, dialkylaminoalkyl, alkoxyalkyl, carboxyalkyl, and the like. In some embodiments, the alkyl group is unsubstituted.

Alkenyl groups include straight and branched chain alkyl groups as defined above, except that at least one double bond exists between two carbon atoms. Alkenyl groups have from 2 to 12 carbon atoms, and typically from 2 to 10 carbons or, in some embodiments, from 2 to 8, 2 to 6, or 2 to 4 carbon atoms. In some embodiments, the alkenyl group has one, two, or three carbon-carbon double bonds. Examples include, but are not limited to vinyl, allyl, $—CH=CH(CH_3)$, $—CH=C(CH_3)_2$, $—C(CH_3)=CH_2$, $—C(CH_3)=CH(CH_3)$, $—C(CH_2CH_3)=CH_2$, among others. Representative substituted alkenyl groups may be mono-substituted or substituted more than once, such as, but not limited to, mono-, di- or tri-substituted with substituents such as those listed above.

The term "(hetero)cycloalkyl" refers to cycloalkyl and heterocycloalkyl groups.

The term "cycloalkyl" refers to saturated cyclic hydrocarbon groups. Unless otherwise indicated, the cycloalkyl group has 3 to 12 ring carbon atoms, alternatively 3 to 8 ring carbon atoms, or alternatively 3 to 6 ring carbon atoms. Preferred cycloalkyl groups include, without limitation, cyclopropyl, cyclobutyl, cyclopentyl, cyclopentenyl, and cyclohexyl. Unless otherwise indicated, the cycloalkyl group is optionally substituted with 1, 2, or 3, preferably 1 or 2, more preferably 1 alkyl group. In some embodiments, the alkyl group may include 1-6 carbon atoms, preferably the alkyl group is unsubstituted and includes 1-4 carbon atoms. In some embodiments, the cycloalkyl group is unsubstituted.

The term "heterocycloalkyl" as used herein refers to non-aromatic ring compounds containing 5 or more ring members, of which at least three are carbon atoms and at least one is a nitrogen atom. In some embodiments, the heterocyclyl group contains 1 or 2 heteroatoms. In some embodiments, the heterocyclyl group may include at least 4 or at least 5 carbon atoms. Typically, the heterocycloalkyl group is unsubstituted.

The term "(hetero)aryl" refers to aryl and heteroaryl groups.

Aryl groups are cyclic aromatic hydrocarbons that do not contain heteroatoms. Aryl groups herein include monocyclic, bicyclic and tricyclic ring systems. Thus, aryl groups include, but are not limited to, phenyl, azulenyl, heptalenyl, biphenyl, fluorenyl, phenanthrenyl, anthracenyl, indenyl, indanyl, pentalenyl, and naphthyl groups. In some embodiments, aryl groups contain 6-14 carbons, and in others from 6 to 12 or even 6-10 carbon atoms in the ring portions of the groups. In some embodiments, the aryl groups are phenyl or naphthyl. Although the phrase "aryl groups" includes groups containing fused rings, such as fused aromatic-aliphatic ring systems (e.g., indanyl, tetrahydronaphthyl, and the like), it does not include aryl groups that have other groups, such as alkyl or halo groups, bonded to one of the ring members. Rather, groups such as tolyl are referred to as substituted aryl groups. Representative substituted aryl groups may be mono-substituted or substituted more than once. For example, monosubstituted aryl groups include, but are not limited to, 2-, 3-, 4-, 5-, or 6-substituted phenyl or naphthyl groups, which may be substituted with substituents such as those listed above.

Heteroaryl groups are aromatic ring compounds containing 5 or more ring members, of which, one or more is a heteroatom such as, but not limited to, N, O, and S. Heteroaryl groups include, but are not limited to, groups such as pyrrolyl, pyrazolyl, triazolyl, tetrazolyl, oxazolyl, isoxazolyl, thiazolyl, pyridinyl, pyridazinyl, pyrimidinyl, pyrazinyl, thiophenyl, benzothiophenyl, furanyl, benzofuranyl, indolyl, azaindolyl (pyrrolopyridinyl), indazolyl, benzimidazolyl, imidazopyridinyl (azabenzimidazolyl), pyrazolopyridinyl, triazolopyridinyl, benzotriazolyl, benzoxazolyl, benzothiazolyl, benzothiadiazolyl, imidazopyridinyl, isoxazolopyridinyl, thianaphthyl, purinyl, xanthinyl, adeninyl, guaninyl, quinolinyl, isoquinolinyl, tetrahydroquinolinyl, quinoxalinyl, and quinazolinyl groups. Heteroaryl groups include fused ring compounds in which all rings are aromatic such as indolyl groups and include fused ring compounds in which only one of the rings is aromatic, such as 2,3-dihydro indolyl groups. Although the phrase "heteroaryl groups" includes fused ring compounds, the phrase does not include heteroaryl groups that have other groups bonded to one of the ring members, such as alkyl groups. Rather, heteroaryl groups with such substitution are referred to as "substituted heteroaryl groups." Representative substituted heteroaryl groups may be substituted one or more times with various substituents such as those listed above.

Alkoxy groups are hydroxyl groups (—OH) in which the bond to the hydrogen atom is replaced by a bond to a carbon atom of a substituted or unsubstituted alkyl group as defined above. Examples of linear alkoxy groups include but are not limited to methoxy, ethoxy, propoxy, butoxy, pentoxy, hexoxy, and the like. Examples of branched alkoxy groups include but are not limited to isopropoxy, sec-butoxy, tert-butoxy, isopentoxy, isohexoxy, and the like. Examples of cycloalkoxy groups include but are not limited to cyclopropyloxy, cyclobutyloxy, cyclopentyloxy, cyclohexyloxy, and the like. Representative substituted alkoxy groups may be substituted one or more times with substituents such as those listed above.

The terms "alkanoyl" and "alkanoyloxy" as used herein can refer, respectively, to —C(O)-alkyl groups and —O—C(O)-alkyl groups, each containing 2-5 carbon atoms. Similarly, "aryloyl" and "aryloyloxy" refer to —C(O)-aryl groups and —O—C(O)-aryl groups.

The terms "aryloxy" and "arylalkoxy" refer to, respectively, a substituted or unsubstituted aryl group bonded to an oxygen atom and a substituted or unsubstituted aralkyl group bonded to the oxygen atom at the alkyl. Examples include but are not limited to phenoxy, naphthyloxy, and benzyloxy. Representative substituted aryloxy and arylalkoxy groups may be substituted one or more times with substituents such as those listed above.

The term "carboxylate" as used herein refers to a —COOH group or its ionized form —$COO^-$.

The term "ester" as used herein refers to —$COOR^{70}$ and —C(O)O-G groups. $R^{70}$ is a substituted or unsubstituted alkyl, cycloalkyl, alkenyl, alkynyl, aryl, aralkyl, heterocyclylalkyl or heterocyclyl group as defined herein. G is a carboxylate protecting group. Carboxylate protecting groups are well known to one of ordinary skill in the art. An extensive list of protecting groups for the carboxylate group functionality may be found in Protective Groups in Organic Synthesis, Greene, T. W.; Wuts, P. G. M., John Wiley & Sons, New York, NY, (3rd Edition, 1999) which can be added or removed using the procedures set forth therein and which is hereby incorporated by reference in its entirety and for any and all purposes as if fully set forth herein.

The term "amide" (or "amido") includes C- and N-amide groups, i.e., —$C(O)NR^{71}R^{72}$, and —$NR^{71}C(O)R^{72}$ groups, respectively. $R^{71}$ and $R^{72}$ are independently hydrogen, or a substituted or unsubstituted alkyl, alkenyl, alkynyl, cycloalkyl, aryl, aralkyl, heterocyclylalkyl or heterocyclyl group as defined herein. Amido groups therefore include but are not limited to carbamoyl groups (—$C(O)NH_2$) and formamide groups (—NHC(O)H). In some embodiments, the amide is —$NR^{71}C(O)$—($C_{1-5}$ alkyl) and the group is termed "carbonylamino," and in others the amide is —NHC(O)-alkyl and the group is termed "alkanoylamino."

The term "nitrile" or "cyano" as used herein refers to the —CN group.

Urethane groups include N- and O-urethane groups, i.e., —$NR^{73}C(O)OR^{74}$ and —$OC(O)NR^{73}R^{74}$ groups, respectively. $R^{73}$ and $R^{74}$ are independently a substituted or unsubstituted alkyl, alkenyl, alkynyl, cycloalkyl, aryl, aralkyl, heterocyclylalkyl, or heterocyclyl group as defined herein. $R^{73}$ may also be H.

The term "amine" (or "amino") as used herein refers to —$NR^{75}R^{76}$ groups, wherein $R^{75}$ and $R^{76}$ are independently hydrogen, or a substituted or unsubstituted alkyl, alkenyl, alkynyl, cycloalkyl, aryl, aralkyl, heterocyclylalkyl or heterocyclyl group as defined herein. In some embodiments, the amine is alkylamino, dialkylamino, arylamino, or alkylarylamino. In other embodiments, the amine is $NH_2$, methylamino, dimethylamino, ethylamino, diethylamino, propylamino, isopropylamino, phenylamino, or benzylamino.

The term "urea" refers to —$NR^{84}$—C(O)—$NR^{85}R^{86}$ groups. $R^{84}$, $R^{85}$, and $R^{86}$ groups are independently hydrogen, or a substituted or unsubstituted alkyl, alkenyl, alkynyl, cycloalkyl, aryl, aralkyl, heterocyclyl, or heterocyclylalkyl group as defined herein.

The term "halogen" or "halo" as used herein refers to bromine, chlorine, fluorine, or iodine. In some embodiments, the halogen is fluorine. In other embodiments, the halogen is chlorine or bromine.

The term "hydroxyl" as used herein can refer to —OH or its ionized form, —O—. A "hydroxyalkyl" group is a hydroxyl-substituted alkyl group, such as HO—$CH_2$—.

The term "imide" refers to —$C(O)NR^{98}C(O)R^{99}$, wherein $R^{98}$ and $R^{99}$ are each independently hydrogen, or a substituted or unsubstituted alkyl, cycloalkyl, alkenyl, alkynyl, aryl aralkyl, heterocyclyl or heterocyclylalkyl group as defined herein.

The term "imine" refers to —$CR^{100}(NR^{101})$ and —$N(CR^{100}R^{101})$ groups, wherein $R^{100}$ and $R^{101}$ are each independently hydrogen or a substituted or unsubstituted alkyl, cycloalkyl, alkenyl, alkynyl, aryl aralkyl, heterocyclyl or heterocyclylalkyl group as defined herein, with the proviso that $R^{100}$ and $R^{101}$ are not both simultaneously hydrogen.

The term "nitro" as used herein refers to an —$NO_2$ group.

The term "acrylate reagent" refers to a reagent with the formula $R^{102}C(O)$— group, where $R^{102}$ is a substituted or unsubstituted alkenyl group as defined herein. Representative acrylate reagents include, but are not limited to $H_2C{=}CHC(O)$—, $H_2C{=}C(CH_3)C(O)$—, $H_2C{=}C(CH_2CH_3)C(O)$—, $H_3CCH{=}CHC(O)$—, $(H_3C)_2C{=}CHC(O)$—, $(H_3C)_2C{=}C(CH_3)C(O)$—, and the like. In some embodiment, the acrylate reagent may refer to the formula $R^{102}C(O)$-LG, where LG is a leaving group as defined herein. Non-limiting examples of acrylate reagents include acryloyl chloride, methacryloyl chloride, acryloyl tosylate, methacryloyl tosylate, acryloyl mesylate, methacryloyl mesylate, acryloyl-O-alkyl, methacryloyl-O-alkyl, and the like. In some embodiment, the acrylate reagent may refer to the formula $R^{102}C(O)$—$OR^{103}$, $R^{102}C(O)$—$NR^{104}R^{105}$, where —$OR^{103}$ and —$NR^{104}R^{105}$ do not leave and $R^{103}$, $R^{104}$, $R^{105}$ are independently hydrogen, or a substituted or unsubstituted alkyl, alkenyl, alkynyl, cycloalkyl, aryl, aralkyl, heterocyclyl, or heterocyclylalkyl group as defined herein.

The term "alkanoyl reagent" refers to the product produced by a nucleophilic Michael addition to an acrylate reagent. Representative alkanoyl reagents include, but are not limited to $H_2C(Nuc)CH_2C(O)$—, $H_2C(Nuc)CH(CH_3)C(O)$—, $H_2C(Nuc)CH(CH_2CH_3)C(O)$—, $H_3CCH(Nuc)CH_2C(O)$—, $(H_3C)_2C(Nuc)CH_2C(O)$—, $(H_3C)_2C(Nuc)CH(CH_3)C(O)$—, and the like, where Nuc is a nucleophile. In some embodiments, the nucleophile may be a nitroalkane.

Groups described herein having two or more points of attachment (i.e., divalent, trivalent, or polyvalent) within the compound of the present technology are designated by use of the suffix, "ene." For example, divalent alkyl groups are alkylene groups, divalent cycloalkyl groups are cycloalkylene groups, and so forth. Substituted groups having a single point of attachment to the compound of the present technology are not referred to using the "ene" designation. Thus, e.g., chloroethyl is not referred to herein as chloroethylene.

As used herein, "substantially free" refers to less than about 2 wt % of the specified component based on the total weight of the composition. In some embodiments, the composition may include less than about 1 wt %, less than about 0.5 wt %, or less than about 0.1 wt %. In any embodiment, the composition may be substantially free of NMP. In some embodiments, the composition may free of detectable amounts of the component. For example, in any embodiment, the composition may be free of detectable amounts of NMP.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member. Thus, for example, a group having 1-3 atoms refers to groups having 1, 2, or 3 atoms. Similarly, a group having 1-5 atoms refers to groups having 1, 2, 3, 4, or 5 atoms, and so forth.

Those of skill in the art will appreciate that compounds of the present technology may exhibit the phenomena of tautomerism, conformational isomerism, geometric isomerism and/or stereoisomerism. As the formula drawings within the specification and claims can represent only one of the possible tautomeric, conformational isomeric, stereochemical or geometric isomeric forms, it should be understood that the present technology encompasses any tautomeric, conformational isomeric, stereochemical and/or geometric isomeric forms of the compounds having one or more of the utilities described herein, as well as mixtures of these various different forms.

"Tautomers" refers to isomeric forms of a compound that are in equilibrium with each other. The presence and concentrations of the isomeric forms will depend on the environment the compound is found in and may be different depending upon, for example, whether the compound is a solid or is in an organic or aqueous solution. For example, in aqueous solution, guanidines may exhibit the following isomeric forms in protic organic solution, also referred to as tautomers of each other:

Because of the limits of representing compounds by structural formulas, it is to be understood that all chemical formulas of the compounds described herein represent all tautomeric forms of compounds and are within the scope of the present technology.

In one aspect, the present technology provides a compound of Formula I, Formula II, Formula III, or Formula IV:

Formula I

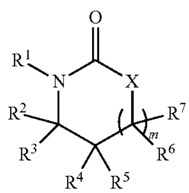

Formula II

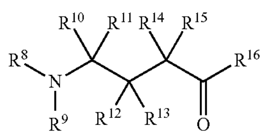

-continued

Formula III

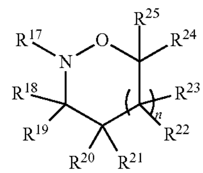

Formula IV

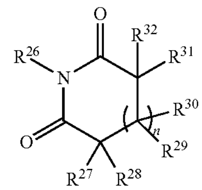

wherein: X may be O or $CR^{33}R^{34}$; $R^1$, $R^8$, $R^9$, $R^{17}$, and $R^{26}$ may each independently be $—CH_3$, $—CH_2CH_3$, $—CH_2CH_2CH_3$, or $—CH(CH_3)_2$; $R^2$, $R^3$, $R^{10}$, $R^{11}$, $R^{14}$, and $R^{15}$ may each independently be —H, $—CH_3$, or $—CH_2CH_3$; $R^6$ and $R^7$ may each independently be absent, —H, $—CH_3$, $—CH_2CH_3$, —CN, $—C(O)N(CH_3)_2$, $—CH_2C(O)N(CH_3)_2$, $—C(O)N(CH_2CH_3)_2$, $—CH_2C(O)N(CH_2CH_3)_2$, $—CO_2CH_3$, or $—CH_2CO_2CH_3$; $R^{16}$ may be $—O—C_1\text{-}C_8$ alkyl, $—O—C_2\text{-}C_8$ (hetero)cycloalkyl, $—O—C_4\text{-}C_{12}$ (hetero)aryl, $—NH_2$, $—NH—C_1\text{-}C_8$ alkyl, $—N(C_1\text{-}C_8\ alkyl)_2$,

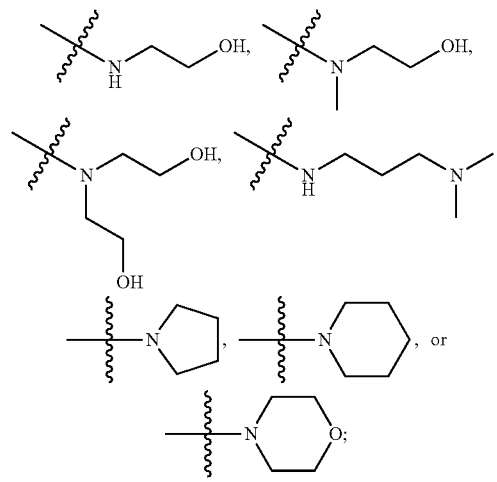

$R^{18}$ and $R^{19}$ may each independently be —H or $—C_1\text{-}C_8$ alkyl; $R^{22}$ and $R^{23}$ may each independently be absent, —H or $—C_1\text{-}C_8$ alkyl; $R^{24}$ and $R^{25}$ may each independently be —H, —CN, $—C_1\text{-}C_8$ alkyl, $—C_2\text{-}C_8$ (hetero)cycloalkyl, $—CH_2—O—C_1\text{-}C_8$ alkyl, $—C(O)—C_1\text{-}C_8$ alkyl, $—C_1\text{-}C_8$ alkylene-C(O)—$C_1\text{-}C_8$ alkyl, $—C(O)—C_2\text{-}C_8$ (hetero)cycloalkyl, $—C_1\text{-}C_8$ alkylene-C(O)—$C_2\text{-}C_8$ (hetero)cycloalkyl, $—CO_2H$, $—CO_2—C_1\text{-}C_8$ alkyl, $—C_1\text{-}C_8$ alkylene-$CO_2—C_1\text{-}C_8$ alkyl, $—CO_2—C_2\text{-}C_8$ (hetero)cycloalkyl, $—C_1\text{-}C_8$ alkylene-$CO_2—C_2\text{-}C_8$ (hetero)cycloalkyl, $—C_1\text{-}C_8$ alkylene-$NH_2$, $—C_1\text{-}C_8$ alkylene-NH—$C_1\text{-}C_8$ alkyl, $—C_1\text{-}C_8$ alkylene-$N(C_1\text{-}C_8\ alkyl)_2$, $—C(O)NH_2$, $—C_1\text{-}C_8$ alkylene-$C(O)NH_2$, $—C(O)NH—C_1\text{-}C_8$ alkyl, $—C(O)N(C_1\text{-}C_8\ alkyl)_2$, $—C_1\text{-}C_8$ alkylene-C(O)NH—$C_1\text{-}C_8$ alkyl, $—C_1\text{-}C_8$ alkylene-$C(O)N(C_1\text{-}C_8\ alkyl)_2$, -(hetero)aryl, -(hetero)cycloalkyl,

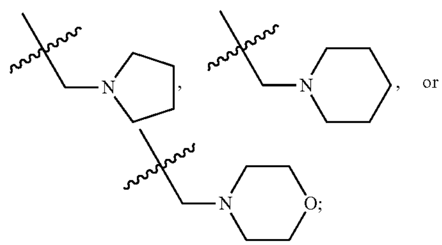

or $R^4$, $R^5$, $R^{12}$, $R^{13}$, $R^{20}$, $R^{21}$, $R^{31}$, $R^{32}$, $R^{33}$, and $R^{34}$ may each independently be —H, —CN, —$C_1$-$C_8$ alkyl, —$C_2$-$C_8$ (hetero)cycloalkyl, —O—$C_1$-$C_8$ alkyl, —$CH_2$—O—$C_1$-$C_8$ alkyl, —C(O)—$C_1$-$C_8$ alkyl, —$C_1$-$C_8$ alkylene-C(O)—$C_1$-$C_8$ alkyl, —C(O)—$C_3$-$C_8$ cycloalkyl, —$C_1$-$C_8$ alkylene-C(O)—$C_2$-$C_8$ (hetero)cycloalkyl, —$CO_2$H, —$CO_2$—$C_1$-$C_8$ alkyl, —$C_1$-$C_8$ alkylene-$CO_2$—$C_1$-$C_8$ alkyl, —$CO_2$—$C_2$-$C_8$ (hetero)cycloalkyl, —$C_1$-$C_8$ alkylene-$CO_2$—$C_2$-$C_8$ (hetero) cycloalkyl, —$NH_2$, —$C_1$-$C_8$ alkylene-$NH_2$, —NH—$C_1$-$C_8$ alkyl, —N($C_1$-$C_8$ alkyl)$_2$, —$C_1$-$C_8$ alkylene-NH—$C_1$-$C_8$ alkyl, —$C_1$-$C_8$ alkylene-N($C_1$-$C_8$ alkyl)$_2$, —C(O)$NH_2$, —$C_1$-$C_8$ alkylene-C(O)$NH_2$, —C(O)NH—$C_1$-$C_8$ alkyl, —C(O)N($C_1$-$C_8$ alkyl)$_2$, —$C_1$-$C_8$ alkylene-C(O)NH—$C_1$-$C_8$ alkyl, —$C_1$-$C_8$ alkylene-C(O)N($C_1$-$C_8$ alkyl)$_2$, -(hetero) aryl, -(hetero)cycloalkyl,

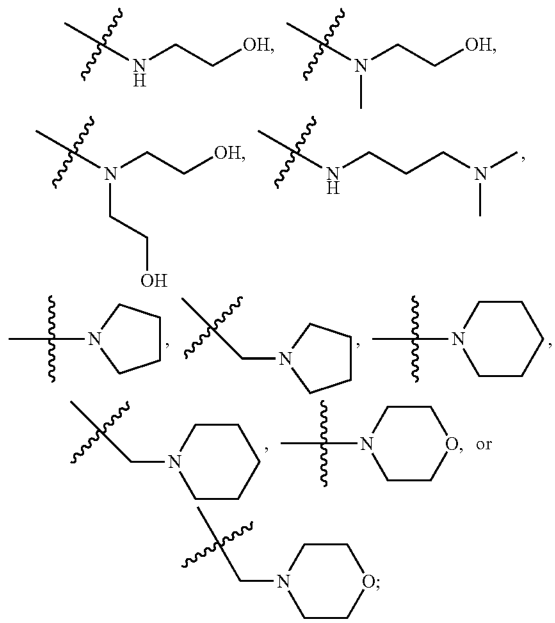

or $R^{27}$ and $R^{28}$ may each independently be —H or —Z—$NR^{35}R^{36}$; $R^{29}$ and $R^{30}$ may each independently be absent, —H, —$CH_3$, or —$CH_2CH_3$; and m, n, and p may each independently be 0 or 1. In any embodiment, Z may be a $C_1$-$C_8$ alkylene and $R^{35}$ and $R^{36}$ may each independently be —H, —$C_1$-$C_8$ alkyl, -(hetero)aryl, -(hetero)cycloalkyl, —$C_1$-$C_8$ alkylene-OH, —$C_1$-$C_8$ alkylene-$NH_2$, —$C_1$-$C_8$ alkylene-NH—$C_1$-$C_8$ alkyl, or —$C_1$-$C_8$ alkylene-N—($C_1$-$C_8$ alkyl)$_2$.

In some embodiments, $R^1$ may be —$CH_3$. In some embodiments, $R^1$ may be —$CH_2CH_3$.

In some embodiments, $R^1$ may be —$CH_2CH_2CH_3$. In some embodiments, $R^1$ may be —$CH(CH_3)_2$.

In some embodiments, $R^8$ may be —$CH_3$. In some embodiments, $R^8$ may be —$CH_2CH_3$.

In some embodiments, $R^8$ may be —$CH_2CH_2CH_3$. In some embodiments, $R^8$ may be —$CH(CH_3)_2$.

In some embodiments, $R^9$ may be —$CH_3$. In some embodiments, $R^9$ may be —$CH_2CH_3$.

In some embodiments, $R^9$ may be —$CH_2CH_2CH_3$. In some embodiments, $R^9$ may be —$CH(CH_3)_2$.

In some embodiments, $R^{17}$ may be —$CH_3$. In some embodiments, $R^{17}$ may be —$CH_2CH_3$.

In some embodiments, $R^{17}$ may be —$CH_2CH_2CH_3$. In some embodiments, $R^{17}$ may be —$CH(CH_3)_2$.

In some embodiments, $R^{26}$ may be —$CH_3$. In some embodiments, $R^{26}$ may be —$CH_2CH_3$.

In some embodiments, $R^{26}$ may be —$CH_2CH_2CH_3$. In some embodiments, $R^{26}$ may be —$CH(CH_3)_2$.

In some embodiments, $R^2$ may be —H. In some embodiments, $R^2$ may be —$CH_3$. In some embodiments, $R^2$ may be —$CH_2CH_3$.

In some embodiments, $R^3$ may be —H. In some embodiments, $R^3$ may be —$CH_3$. In some embodiments, $R^3$ may be —$CH_2CH_3$.

In certain embodiments, $R^2$ and $R^3$ together may include at least 1 carbon atom. In certain embodiments, $R^2$ and $R^3$ together may include at least 2 carbon atoms.

In some embodiments, $R^{10}$ may be —H. In some embodiments, $R^{10}$ may be —$CH_3$. In some embodiments, $R^{10}$ may be —$CH_2CH_3$.

In some embodiments, $R^{11}$ may be —H. In some embodiments, $R^{11}$ may be —$CH_3$. In some embodiments, $R^{11}$ may be —$CH_2CH_3$.

In certain embodiments, $R^{10}$ and $R^{11}$ together may include at least 1 carbon atom. In certain embodiments, $R^{10}$ and $R^{11}$ together may include at least 2 carbon atoms.

In some embodiments, $R^{14}$ may be —H. In some embodiments, $R^{14}$ may be —$CH_3$. In some embodiments, $R^{14}$ may be —$CH_2CH_3$.

In some embodiments, $R^{15}$ may be —H. In some embodiments, $R^{15}$ may be —$CH_3$. In some embodiments, $R^{15}$ may be —$CH_2CH_3$.

In certain embodiments, $R^{14}$ and $R^{15}$ together may include at least 1 carbon atom. In certain embodiments, $R^{14}$ and $R^{15}$ together may include at least 2 carbon atoms.

In some embodiments, m, n, and p may each be 0 and $R^6$, $R^7$, $R^{22}$, $R^{23}$, $R^{29}$, and $R^{30}$ may each be absent. In other embodiments, m, n, and p may each be 1.

In certain embodiments, m is 1. In some embodiments, $R^6$ may be —H. In some embodiments, $R^6$ may be —$CH_3$. In some embodiments, $R^6$ may be —$CH_2CH_3$. In some embodiments, $R^6$ may be —CN, —C(O)N$(CH_3)_2$, —$CH_2$C(O)N$(CH_3)_2$, —$CO_2CH_3$, or —$CH_2CO_2CH_3$. In some embodiments, $R^6$ may be —$CO_2CH_3$ or —$CH_2CO_2CH_3$. In some embodiments, $R^6$ may be —$CO_2CH_3$. In some embodiments, $R^7$ may be —H. In some embodiments, $R^7$ may be —$CH_3$. In some embodiments, $R^7$ may be —$CH_2CH_3$. In some embodiments, $R^7$ may be —CN, —C(O)N$(CH_3)_2$, —$CH_2$C(O)N$(CH_3)_2$, —$CO_2CH_3$, or —$CH_2CO_2CH_3$. In some embodiments, $R^7$ may be —$CO_2CH_3$ or —$CH_2CO_2CH_3$. In some embodiments, $R^7$ may be —$CO_2CH_3$.

In certain embodiments, n is 1. In some embodiments, $R^{22}$ may be —H. In some embodiments, $R^{22}$ may be —$CH_3$. In some embodiments, $R^{22}$ may be —$CH_2CH_3$. In some embodiments, $R^{23}$ may be —H. In some embodiments, $R^{23}$ may be —$CH_3$. In some embodiments, $R^{23}$ may be —$CH_2CH_3$.

In certain embodiments, p is 1. In some embodiments, $R^{29}$ may be —H. In some embodiments, $R^{29}$ may be —$CH_3$. In some embodiments, $R^{29}$ may be —$CH_2CH_3$. In some embodiments, $R^{30}$ may be —H. In some embodiments, $R^{30}$ may be —$CH_3$. In some embodiments, $R^{30}$ may be —$CH_2CH_3$.

In any embodiment, $R^4$, $R^5$, $R^{12}$, $R^{13}$, $R^{20}$, $R^{21}$, $R^{31}$, $R^{32}$, $R^{33}$, and $R^{34}$ may each independently be —H, —CN, —$CH_3$, —$CH_2CH_3$, —$OCH_3$, —$OCH_2CH_3$, —C(O)$CH_3$, —C(O)$CH_2CH_3$, —$CH_2$C(O)$CH_3$, —$CH_2COCH_2CH_3$, —$C(O)_2H$, —$CO_2CH_3$, —$CO_2CH_2CH_3$, —$CH_2CO_2CH_3$, —$CH_2CO_2CH_2CH_3$, —$NH_2$, —CH($CH_3$)$NH_2$, —$CH_2$CH($CH_3$)$NH_2$, —CH($CH_3$)$CH_2NH_2$, —C$(CH_3)_2NH_2$, —$CH_2$C$(CH_3)_2NH_2$, —C$(CH_3)_2CH_2NH_2$, —$CH_2NH_2$, —$CH_2CH_2NH_2$, —$CH_2CH_2CH_2NH_2$, —N$(CH_3)_2$, —N$(CH_2CH_3)_2$, —$CH_2$N$(CH_3)_2$, —$CH_2$N$(CH_2CH_3)_2$, —C(O)N$(CH_3)_2$, —C(O)N$(CH_2CH_3)_2$, —$CH_2$C(O)$NH_2$, —$CH_2$C(O)N$(CH_3)_2$, —$CH_2$C(O)N$(CH_2CH_3)_2$, $C_4$-$C_{12}$ (hetero)aryl, $C_2$-$C_8$ (hetero)cycloalkyl,

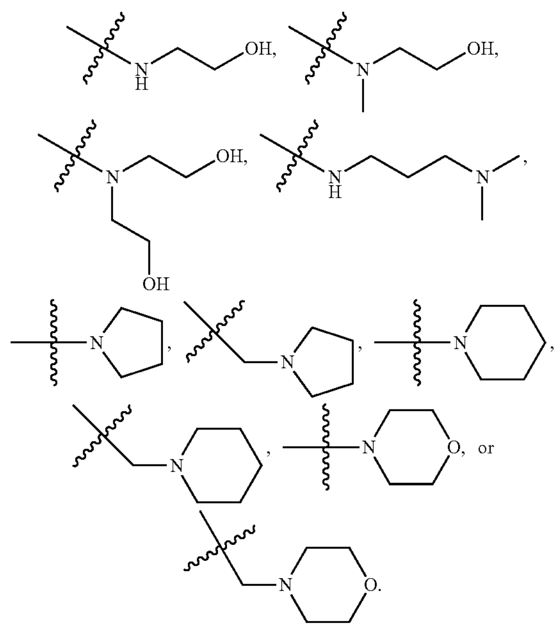

In some embodiments, $R^4$, $R^5$, $R^{12}$, $R^{13}$, $R^{20}$, $R^{21}$, $R^{31}$, $R^{32}$, $R^{33}$, and $R^{34}$ may each be —H. In some embodiments, $R^4$, $R^5$, $R^{12}$, $R^{13}$, $R^{20}$, $R^{21}$, $R^{31}$, $R^{32}$, $R^{33}$, and $R^{34}$ may each independently be —H or —CN. In some embodiments, $R^4$, $R^5$, $R^{12}$, $R^{13}$, $R^{20}$, $R^{21}$, $R^{31}$, $R^{32}$, $R^{33}$, and $R^{34}$ may each independently be —H, —$CH_3$, or —$CH_2CH_3$. In some embodiments, $R^4$, $R^5$, $R^{12}$, $R^{13}$, $R^{20}$, $R^{21}$, $R^{31}$, $R^{32}$, $R^{33}$, and $R^{34}$ may each independently be —H, —$OCH_3$, or —$OCH_2CH_3$. In some embodiments, $R^4$, $R^5$, $R^{12}$, $R^{13}$, $R^{20}$, $R^{21}$, $R^{31}$, $R^{32}$, $R^{33}$, and $R^{34}$ may each independently be —H, —C(O)$CH_3$, —C(O)$CH_2CH_3$, —$CH_2$C(O)$CH_3$, or —$CH_2$C(O)$CH_2CH_3$. In some embodiments, $R^4$, $R^5$, $R^{12}$, $R^{13}$, $R^{20}$, $R^{21}$, $R^{31}$, $R^{32}$, $R^{33}$, and $R^{34}$ may each independently be —H, —$C(O)_2H$, —$CO_2CH_3$, —$CO_2CH_2CH_3$, —$CH_2CO_2CH_3$, or —$CH_2CO_2CH_2CH_3$. In some embodiments, $R^4$, $R^5$, $R^{12}$, $R^{13}$, $R^{20}$, $R^{21}$, $R^{31}$, $R^{32}$, $R^{33}$, and $R^{34}$ may each independently be —H, —$NH_2$, —CH($CH_3$)$NH_2$, —$CH_2$CH($CH_3$)$NH_2$, —CH($CH_3$)$CH_2NH_2$, —C$(CH_3)_2NH_2$, —$CH_2$C$(CH_3)_2NH_2$, —C$(CH_3)_2CH_2NH_2$, —$CH_2NH_2$, —$CH_2CH_2NH_2$, —$CH_2CH_2CH_2NH_2$, —N$(CH_3)_2$, —N$(CH_2CH_3)_2$, —$CH_2$N$(CH_3)_2$, or —$CH_2$N$(CH_2CH_3)_2$. In some embodiments, $R^4$, $R^5$, $R^{12}$, $R^{13}$, $R^{20}$, $R^{21}$, $R^{31}$, $R^{32}$, $R^{33}$, and $R^{34}$ may each independently be —H, —C(O)N$(CH_3)_2$, —C(O)N$(CH_2CH_3)_2$, —$CH_2$C(O)$NH_2$, —$CH_2$C(O)N$(CH_3)_2$, or —$CH_2$C(O)N$(CH_2CH_3)_2$. In some embodiments, $R^4$, $R^5$, $R^{12}$, $R^{13}$, $R^{20}$, $R^{21}$, $R^{31}$, $R^{32}$, $R^{33}$, and $R^{34}$ may each independently be —H, $C_4$-$C_{12}$ (hetero)aryl, or $C_2$-$C_8$ (hetero)cycloalkyl. In some embodiments, $R^4$, $R^5$, $R^{12}$, $R^{13}$, $R^{20}$, $R^{21}$, $R^{31}$, $R^{32}$, $R^{33}$, and $R^{34}$ may each independently be —H,

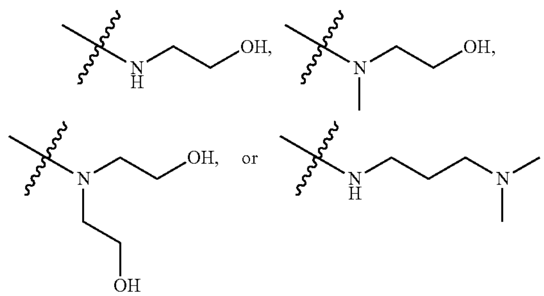

In some embodiments, $R^4$, $R^5$, $R^{12}$, $R^{13}$, $R^{20}$, $R^{21}$, $R^{31}$, $R^{32}$, $R^{33}$, and $R^{34}$ may each independently be —H,

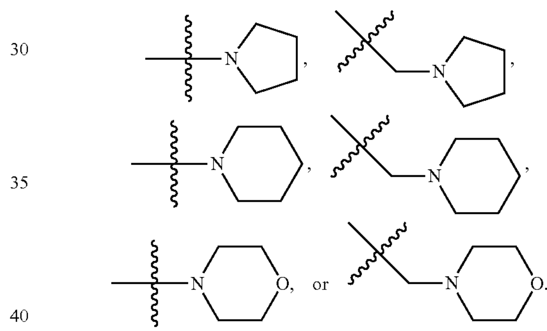

In certain embodiments, the compound is a compound of Formula I. In some embodiments, $R^4$, $R^5$, $R^{33}$, and $R^{34}$ may each independently be —H, —CN, —$CH_3$, —$CH_2CH_3$, —C(O)$CH_3$, —C(O)$CH_2CH_3$, —$CH_2$C(O)$CH_3$, —$CH_2COCH_2CH_3$, —$CO_2H$, —$CO_2CH_3$, —$CO_2CH_2CH_3$, —$CH_2CO_2CH_3$, —$CH_2CO_2CH_2CH_3$, —C(O)N$(CH_3)_2$, —C(O)N$(CH_2CH_3)_2$, —$CH_2$C(O)$NH_2$, —$CH_2$C(O)N$(CH_3)_2$, —$CH_2$C(O)N$(CH_2CH_3)_2$,

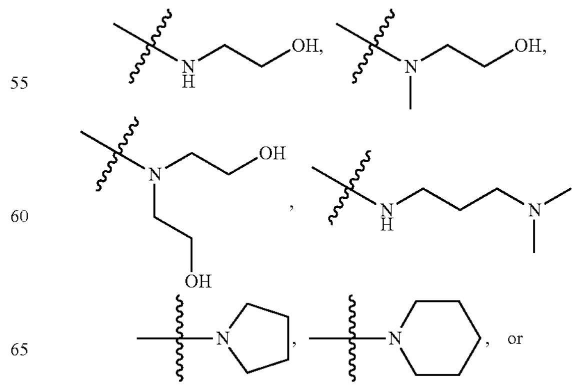

-continued

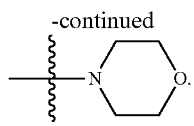

In some embodiments, $R^4$, $R^5$, $R^{33}$, and $R^{34}$ may each independently be —H, —CN, —$CH_3$, —$CH_2CH_3$, —C(O)$CH_3$, —$CH_2C(O)CH_3$, —$CO_2H$, —$CO_2CH_3$, —$CH_2CO_2CH_3$, or —C(O)N$(CH_3)_2$. In certain embodiments, at least one of $R^4$, $R^5$, $R^{33}$, and $R^{34}$ may be not H. In other embodiments, $R^4$, $R^5$, $R^{33}$, and $R^{34}$ may each be —H.

In some embodiments, $R^4$ may be —H.

In some embodiments, $R^5$ may be —H, —$CO_2H$, or —$CO_2CH_3$.

In some embodiments, $R^4$ may be —H and least one of $R^5$, $R^{33}$, and $R^{34}$ may be not —H.

In some embodiments, $R^4$ and $R^5$ may be —H.

In some embodiments, X may be $CR^{33}R^{34}$. In some embodiments, $R^{33}$ may be —H or —$CO_2CH_3$. In some embodiments, $R^{34}$ may be —H, —CN, —$CH_3$, —C(O)$CH_3$, —$CO_2CH_3$, —$CH_2CO_2CH_3$, or —C(O)N$(CH_3)_2$. In other embodiments, X may be O.

In some embodiments, $R^6$ and $R^7$ may each independently be —H, —$CH_3$, —$CH_2CH_3$, —CN, —C(O)N$(CH_3)_2$, —$CH_2C(O)N(CH_3)_2$, —C(O)N$(CH_2CH_3)_2$, —$CH_2C(O)N(CH_2CH_3)_2$, —$CO_2CH_3$, or —$CH_2CO_2CH_3$. In some embodiments, $R^6$ may be —H and $R^7$ may be —CN, —C(O)N$(CH_3)_2$, —$CH_2C(O)N(CH_3)_2$, —C(O)N$(CH_2CH_3)_2$, —$CH_2C(O)N(CH_2CH_3)_2$, —$CO_2CH_3$, or —$CH_2CO_2CH_3$. In some embodiments, $R^6$ may be —H and $R^7$ may be —$CO_2CH_3$.

In certain embodiments, $R^4$, $R^5$, $R^{33}$, and $R^{34}$ may each be —H and at least one of $R^6$ and $R^7$ may not be —H.

In some embodiments, $R^1$ may be —$CH_3$ or —$CH_2CH_3$, $R^2$ may be H or —$CH_3$, $R^3$ may be —$CH_3$ or —$CH_2CH_3$, $R^4$ may be —H, $R^5$ may be —H or —$CO_2CH_3$, and m may be 0. In some embodiments, $R^1$ may be —$CH_3$ or —$CH_2CH_3$, $R^2$ may be H or —$CH_3$, $R^3$ may be —$CH_3$ or —$CH_2CH_3$, $R^4$ may be —H, $R^5$ may be —H, X may be O, and m may be 0. In some embodiments, $R^1$ may be —$CH_3$ or —$CH_2CH_3$, $R^2$ may be H or —$CH_3$, $R^3$ may be —$CH_3$ or —$CH_2CH_3$, $R^4$ may be —H, $R^5$ may be —H, —$CO_2CH_3$, or —CN, X may be $CR^{33}R^{34}$, $R^{33}$ may be H, $R^{34}$ may be —H, —$CH_3$, —$CO_2CH_3$, or —CN, and m may be 0.

In some embodiments, $R^2$ and $R^3$ together preferably contain at least two carbon atoms.

In some embodiments, at least one of $R^4$, $R^5$, $R^{33}$, and $R^{34}$ may be —$CH_3$, —$CO_2CH_3$, or —CN. In some embodiments, one of $R^4$, $R^5$, $R^{33}$, and $R^{34}$ may be —$CH_3$, —$CO_2CH_3$, or —CN and the remainder may be —H.

In some embodiments, the compound of Formula I may be one of the following compounds:

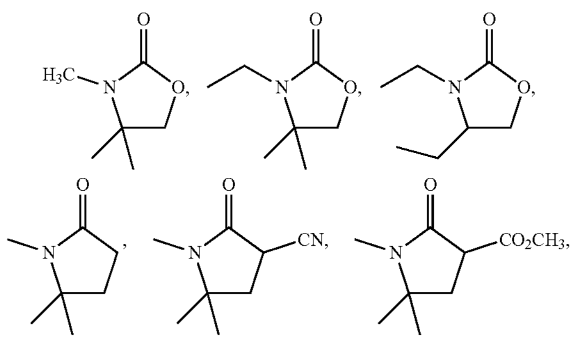

-continued

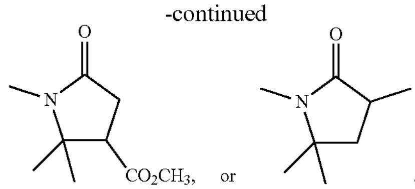

or

In some embodiments, the compound of Formula I may be one of the following compounds:

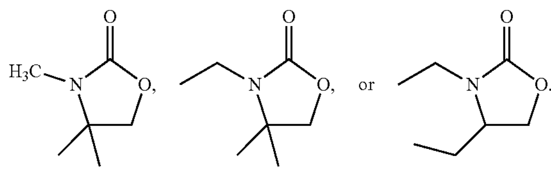

or

In some embodiments, the compound of Formula I may be one of the following compounds:

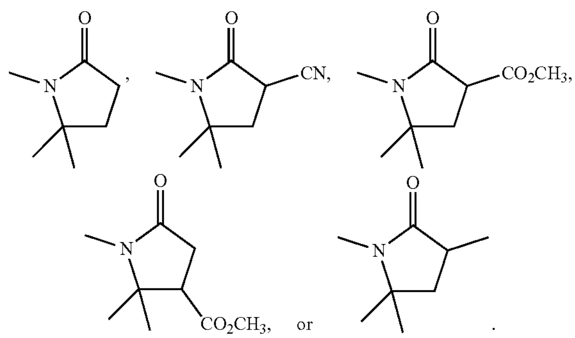

or

In some embodiments, the $R^4$ and $R^5$ together are not a divalent group (e.g., C=$CH_2$).

In certain embodiments, the compound is a compound of Formula II.

In some embodiments, $R^{12}$ may be —H.

In some embodiments, $R^{13}$ may be —H, —$CH_3$, —$CH_2CH_3$, —CN, —C(O)N$(CH_3)_2$, —$CH_2C(O)N(CH_3)_2$, —C(O)N$(CH_2CH_3)_2$, —$CH_2C(O)N(CH_2CH_3)_2$, —$CO_2CH_3$, or —$CH_2CO_2CH_3$. In some embodiments, $R^{13}$ may be —H or —$CH_3$.

In some embodiments, $R^{14}$ may be —H. In other embodiments, $R^{14}$ may be —$CH_3$.

In some embodiments, $R^{16}$ may be —$OCH_3$, —$OCH_2CH_3$, —N$(CH_3)_2$, —N$(CH_2CH_3)_2$,

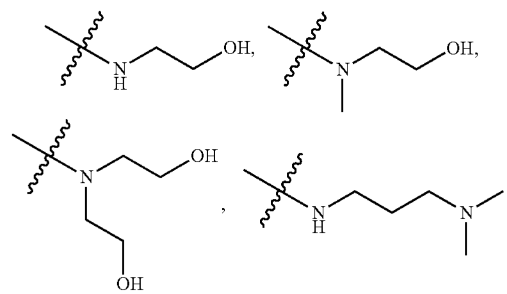

-continued

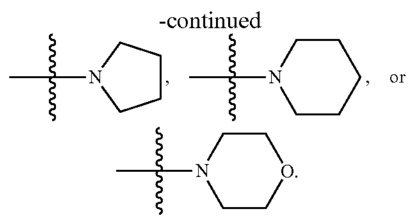

In some embodiments, $R^{16}$ may be —$OCH_3$, —$N(CH_3)_2$, or

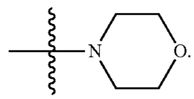 [SMILES: *N1CCOCC1]

In some embodiments, $R^8$ may be —$CH_3$ or —$CH_2CH_3$. In some embodiments, $R^9$ may be —$CH_3$ or —$CH_2CH_3$. In some embodiments, $R^8$ and $R^9$ may be —$CH_3$. In some embodiments, $R^8$ and $R^9$ may be —$CH_2CH_3$. In some embodiments, $R^{10}$ may be —H or —$CH_3$. In some embodiments, $R^{11}$ may be —$CH_3$ or —$CH_2CH_3$. In some embodiments, $R^{10}$ may be —H and $R^{11}$ may be —$CH_2CH_3$. In some embodiments, $R^{10}$ and $R^{11}$ may be —$CH_3$. In some embodiments, $R^{12}$, $R^{13}$, $R^{14}$, and $R^{15}$ may each independently be —H or —$CH_3$. In some embodiments, $R^{12}$, $R^{13}$, $R^{14}$, and $R^{15}$ may each be —H. In some embodiments, at least one of $R^{12}$, $R^{13}$, $R^{14}$, and $R^{15}$ may be —$CH_3$. In some embodiments, $R^{12}$, $R^{13}$, $R^{14}$, and $R^{15}$ may each be —$CH_3$. In some embodiments, $R^{12}$ and $R^{13}$ may be —H and $R^{14}$ and $R^{15}$ may each be —$CH_3$. In some embodiments, $R^{12}$ and $R^{13}$ may be —$CH_3$ and $R^{14}$ and $R^{15}$ may each be —H.

In some embodiments, the compound of Formula II may be one of the following compounds:

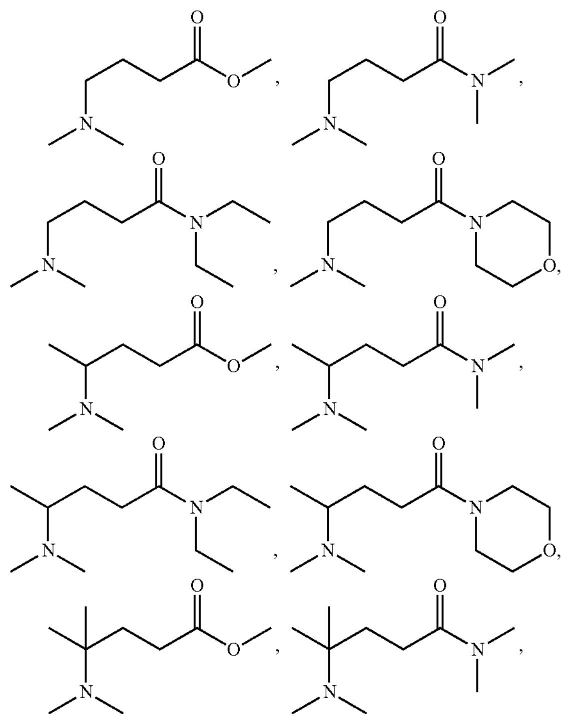

-continued

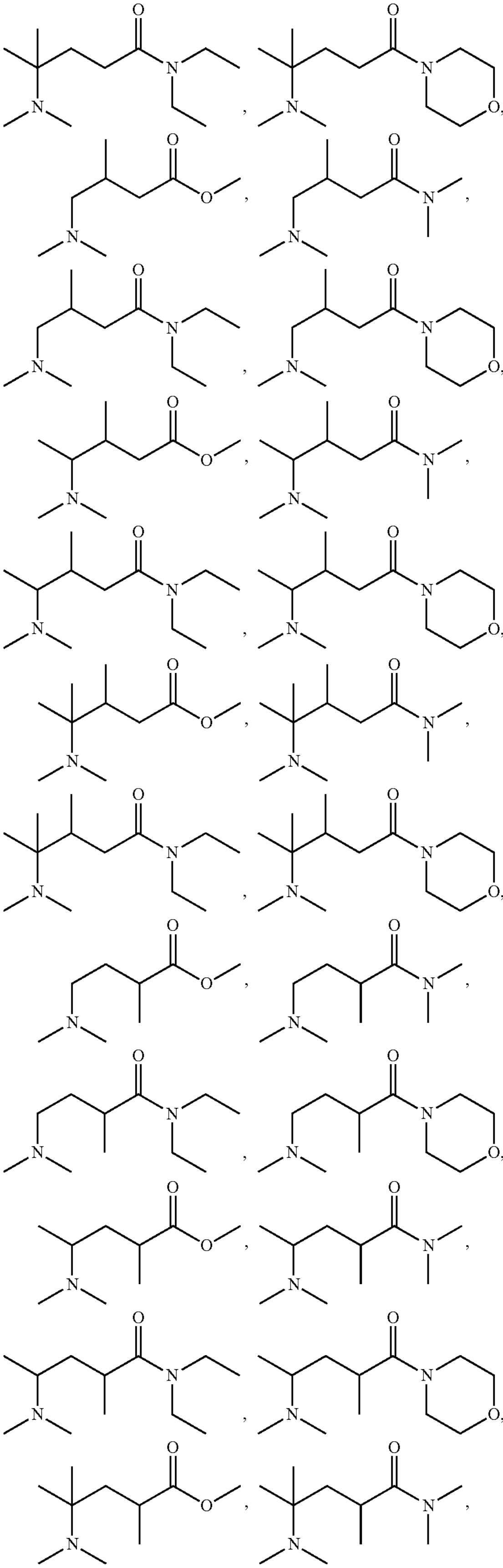

-continued
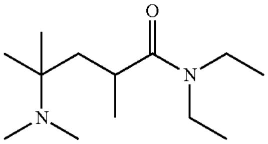, 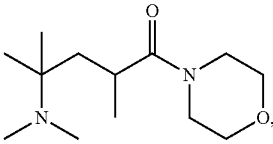
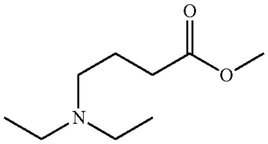, 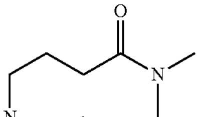,
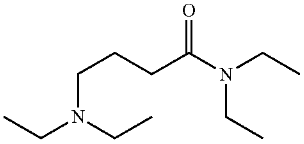
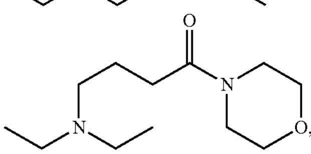
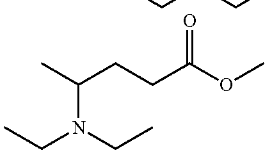, 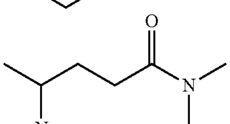,
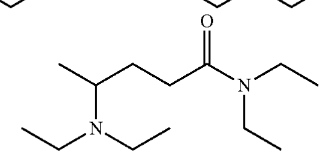
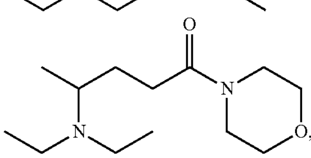
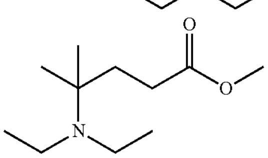, 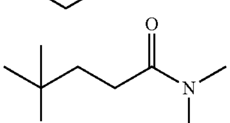,
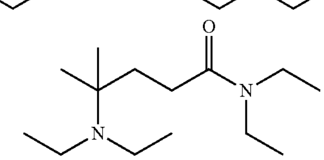
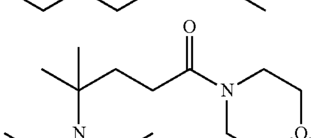
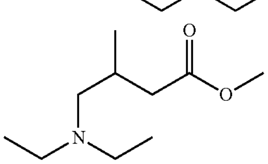, 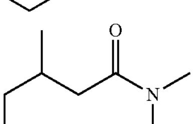,
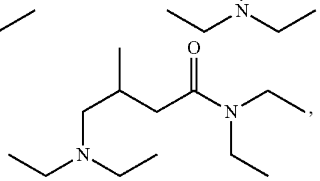
-continued
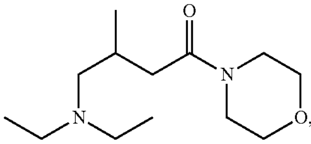
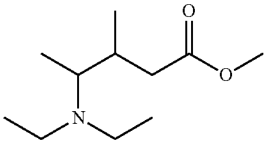, 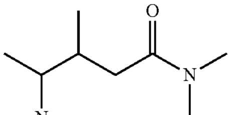,
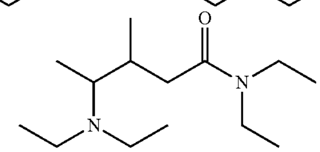
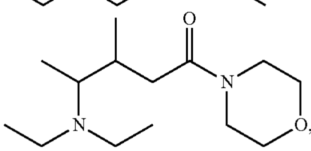
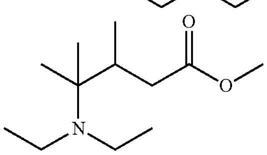, 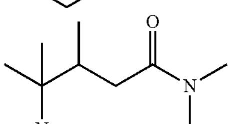,
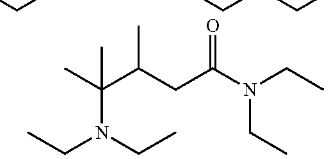
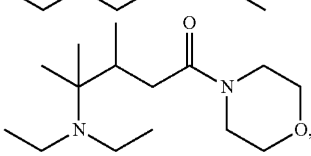
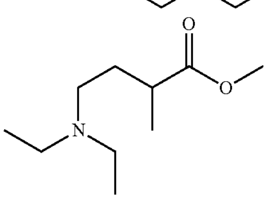, 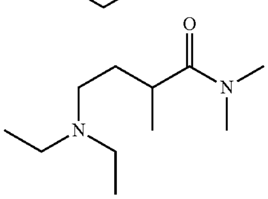,
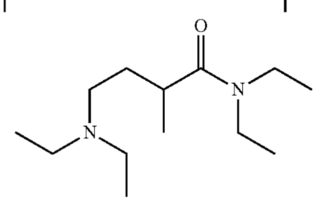
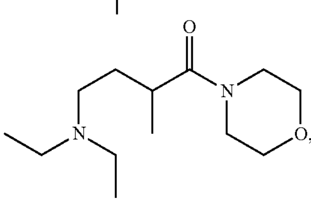
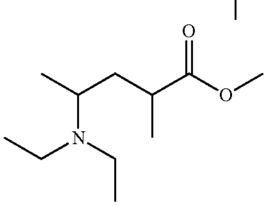, 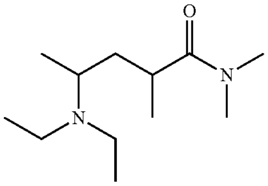, -continued
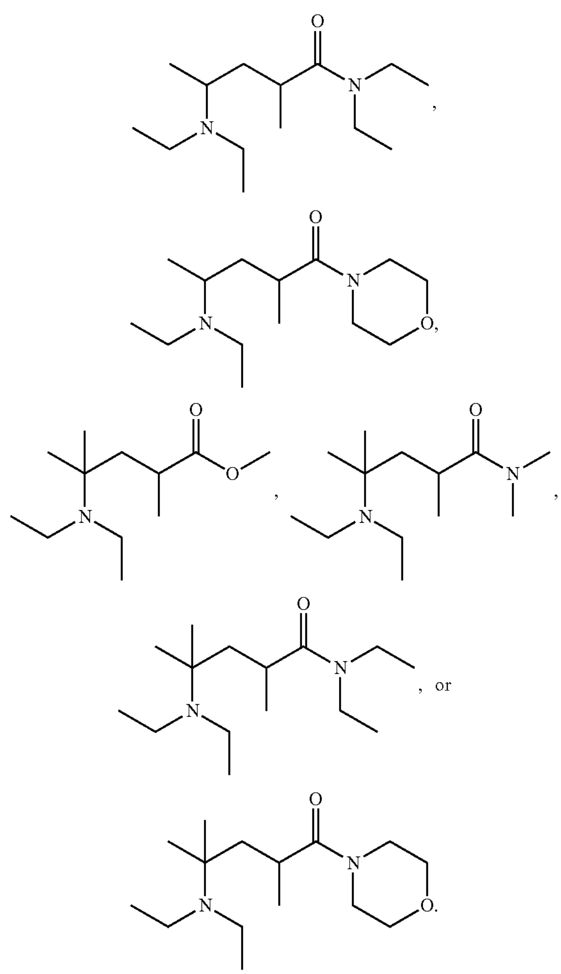
In some embodiments, the compound of Formula II may be one of the following compounds:
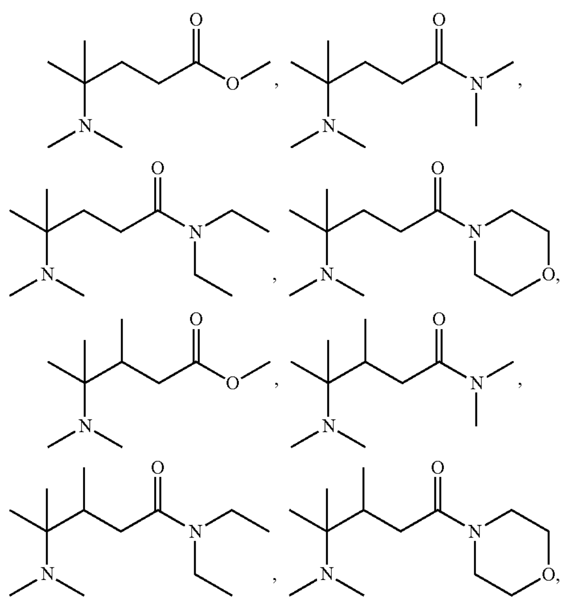
-continued
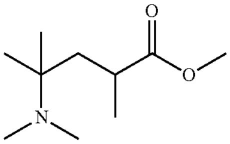, 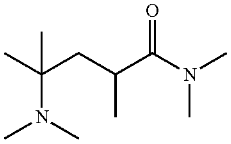,
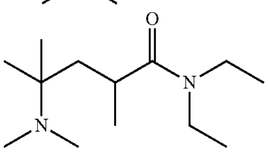, 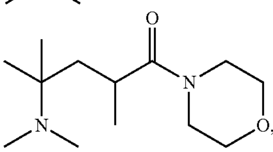
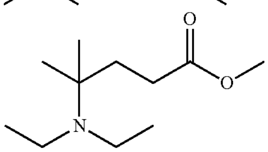, 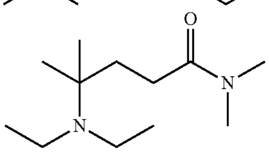,
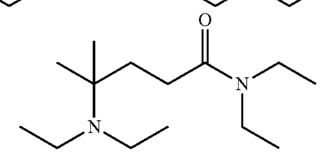,
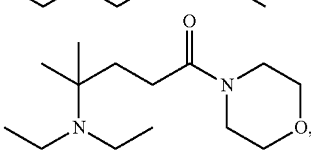
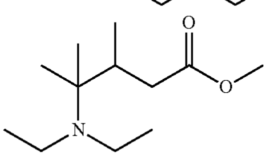, 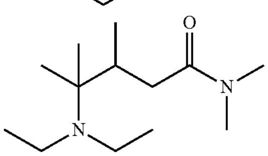,
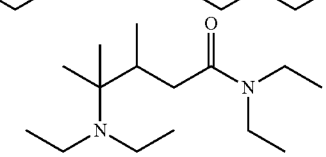,
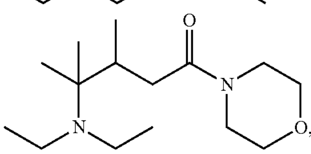
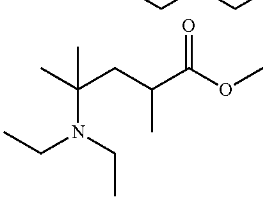, 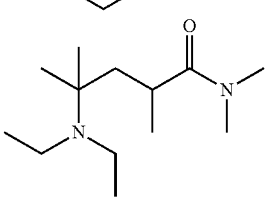,
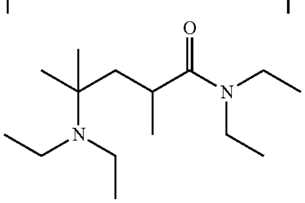, or
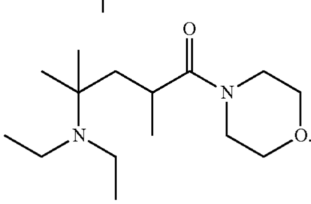

In some embodiments, the compound of Formula II may be one of the following compounds:

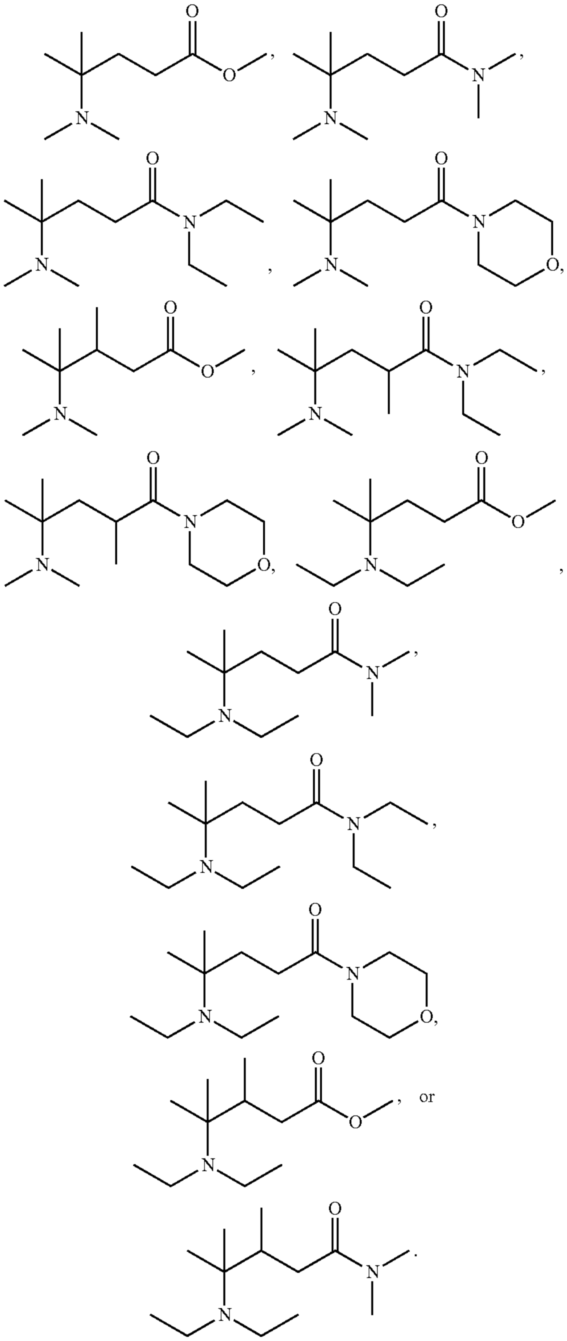

In some embodiments, the compound of Formula II may be one of the following compounds:

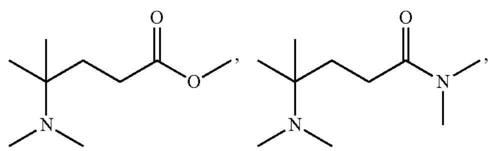

-continued

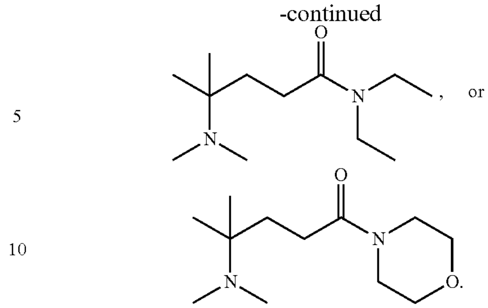

In some embodiments, the compound of Formula II may be one of the following compounds:

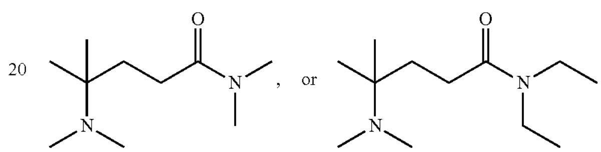

In certain embodiments, the compound is a compound of Formula III. In some embodiments, $R^{18}$ and $R^{19}$ may each independently be —H or —$C_1$-$C_6$ alkyl. In some embodiments, $R^{18}$ and $R^{19}$ may each independently be —H or —$C_1$-$C_4$ alkyl. In some embodiments, $R^{18}$ and $R^{19}$ may each independently be —H or —$C_1$-$C_3$ alkyl. In some embodiments, $R^{18}$ may be —H. In some embodiments, $R^{19}$ may be —H or —$CH_3$.

In some embodiments, $R^{20}$ and $R^{21}$ may each independently be —H, —CN, —$CH_3$, —$CH_2CH_3$, —$C(O)CH_3$, —$C(O)CH_2CH_3$, —$CH_2C(O)CH_3$, —$CH_2COCH_2CH_3$, —$C(O)_2H$, —$CO_2CH_3$, —$CO_2CH_2CH_3$, —$CH_2CO_2CH_3$, —$CH_2CO_2CH_2CH_3$, —$C(O)N(CH_3)_2$, —$C(O)N(CH_2CH_3)_2$, —$CH_2C(O)NH_2$, —$CH_2C(O)N(CH_3)_2$, —$CH_2C(O)N(CH_2CH_3)_2$, —$C_4$-$C_{12}$ (hetero)aryl, —$C_2$-$C_8$ (hetero)cycloalkyl,

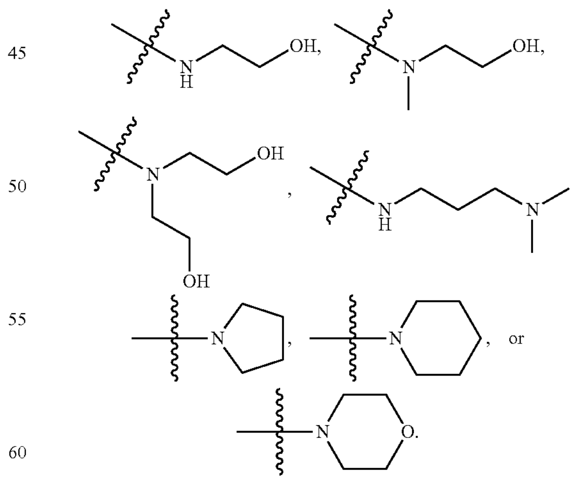

In some embodiments, $R^{24}$ and $R^{25}$ may each independently be —H, —CN, —$C_1$-$C_4$ alkyl, —$C_2$-$C_6$ (hetero) cycloalkyl, —$CH_2$—O—$C_1$-$C_4$ alkyl, —C(O)—$C_1$-$C_4$ alkyl, —$C_1$-$C_4$ alkylene-C(O)—$C_1$-$C_4$ alkyl, —C(O)—$C_2$-$C_6$ (hetero)cycloalkyl, —$C_1$-$C_4$ alkylene-C(O)—$C_2$-$C_6$ (hetero)cycloalkyl, $-CO_2H$, $-CO_2-C_1$-$C_4$ alkyl, $-C_1$-$C_4$ alkylene-$CO_2-C_1$-$C_4$ alkyl, $-CO_2-C_2$-$C_6$ (hetero)cycloalkyl, $-C_1$-$C_4$ alkylene-$CO_2-C_2$-$C_6$ (hetero)cycloalkyl, $-C_1$-$C_4$ alkylene-$NH_2$, $-C_1$-$C_4$ alkylene-NH$-C_1$-$C_4$ alkyl, $-C_1$-$C_4$ alkylene-N($C_1$-$C_4$ alkyl)$_2$, $-C(O)NH_2$, $-C_1$-$C_4$ alkylene-$C(O)NH_2$, $-C(O)NH-C_1$-$C_4$ alkyl, $-C(O)N(C_1$-$C_4$ alkyl)$_2$, $-C_1$-$C_4$ alkylene-C(O)NH$-C_1$-$C_4$ alkyl, $-C_1$-$C_4$ alkylene-C(O)N($C_1$-$C_4$ alkyl)$_2$, $-C_4$-$C_{12}$ (hetero)aryl, or $-C_3$-$C_6$ (hetero)cycloalkyl.

In some embodiments, $R^{20}$, $R^{21}$, $R^{24}$, and $R^{25}$ may each independently be —H, —CN, $-CH_3$, $-CH_2CH_3$, $-C(O)CH_3$, $-CH_2C(O)CH_3$, $-CO_2CH_3$, $-CH_2CO_2CH_3$, $-C(O)N(CH_3)_2$, phenyl, cyclopentyl, or cyclohexyl.

In some embodiments, $R^{20}$ may be —H, $-CH_3$, $-CH_2CH_3$, $-CO_2CH_3$, or phenyl. In some embodiments, $R^{20}$ may be —H. In some embodiments, $R^{21}$ may be —H, $-CH_3$, $-CH_2CH_3$, $-CO_2CH_3$, or phenyl. In some embodiments, $R^{21}$ may be $-CH_3$, $-CH_2CH_3$, $-CO_2CH_3$, or phenyl. In some embodiments, n may be 0 and $R^{22}$ and $R^{23}$ may be absent. In other embodiments, n may be 1 and $R^{22}$ and $R^{23}$ may be —H.

In some embodiments, $R^{24}$ may be —H, —CN, $-C(O)CH_3$, $-CO_2CH_3$, $-CH_2CO_2CH_3$, $-C(O)N(CH_3)_2$, phenyl, cyclopentyl, or cyclohexyl. In some embodiments, $R^{24}$ may be —H, —CN, $-C(O)CH_3$, $-CO_2CH_3$, $-CH_2CO_2CH_3$, $-C(O)N(CH_3)_2$, phenyl, cyclopentyl, or cyclohexyl. In some embodiments, $R^{25}$ may be —CN, $-C(O)CH_3$, $-CO_2CH_3$, $-CH_2CO_2CH_3$, $-C(O)N(CH_3)_2$, phenyl, cyclopentyl, or cyclohexyl.

In some embodiments, $R^{18}$ may be —H, $R^{19}$ may be —H or $-CH_3$, $R^{20}$ may be —H, $R^{21}$ may be —H or $-CO_2CH_3$, $R^{22}$ and $R^{23}$ may be absent, $R^{24}$ may be —H or $-CO_2CH_3$, and $R^{25}$ may be —CN, $-C(O)CH_3$, $-CO_2CH_3$, $-CH_2CO_2CH_3$, or $-C(O)N(CH_3)_2$. In some embodiments, $R^{24}$ may be —H and $R^{25}$ may be —CN, $-C(O)CH_3$, $-CO_2CH_3$, or $-C(O)N(CH_3)_2$. In some embodiments, $R^{24}$ may be $-CO_2CH_3$ and $R^{25}$ may be —CN, $-CO_2CH_3$, or $-CH_2CO_2CH_3$.

In some embodiments, $R^{24}$ may be —H, $-CH_3$, $-CH_2CH_3$, $-CO_2CH_3$, or phenyl. In some embodiments, $R^{24}$ may be —H. In some embodiments, $R^{25}$ may be —H, $-CH_3$, $-CH_2CH_3$, $-CO_2CH_3$, or phenyl. In some embodiments, $R^{25}$ may be $-CH_3$, $-CH_2CH_3$, $-CO_2CH_3$, or phenyl. In some embodiments, n may be 0 and $R^{22}$ and $R^{23}$ may be absent. In other embodiments, n may be 1 and $R^{22}$ and $R^{23}$ may be —H.

In some embodiments, $R^{20}$ may be —H, —CN, $-C(O)CH_3$, $-CO_2CH_3$, $-CH_2CO_2CH_3$, $-C(O)N(CH_3)_2$, phenyl, cyclopentyl, or cyclohexyl. In some embodiments, $R^{20}$ may be —H, —CN, $-C(O)CH_3$, $-CO_2CH_3$, $-CH_2CO_2CH_3$, $-C(O)N(CH_3)_2$, phenyl, cyclopentyl, or cyclohexyl. In some embodiments, $R^{21}$ may be —CN, $-C(O)CH_3$, $-CO_2CH_3$, $-CH_2CO_2CH_3$, $-C(O)N(CH_3)_2$, phenyl, cyclopentyl, or cyclohexyl.

In some embodiments, $R^{18}$ may be —H, $R^{19}$ may be —H or $-CH_3$, $R^{24}$ may be —H, $R^{25}$ may be —H or $-CO_2CH_3$, $R^{22}$ and $R^{23}$ may be absent, $R^{20}$ may be —H or $-CO_2CH_3$, and $R^{21}$ may be —CN, $-C(O)CH_3$, $-CO_2CH_3$, $-CH_2CO_2CH_3$, or $-C(O)N(CH_3)_2$. In some embodiments, $R^{20}$ may be —H and $R^{21}$ may be —CN, $-C(O)CH_3$, $-CO_2CH_3$, or $-C(O)N(CH_3)_2$. In some embodiments, $R^{20}$ may be $-CO_2CH_3$ and $R^{21}$ may be —CN, $-CO_2CH_3$, or $-CH_2CO_2CH_3$.

In some embodiments, the compound of Formula III may be one of the following compounds:

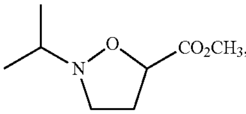, 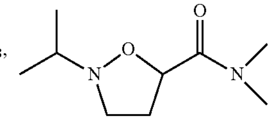,

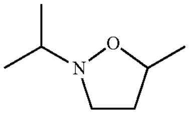, 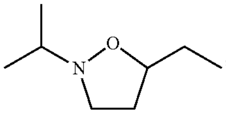,

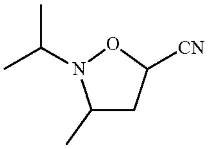, 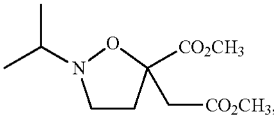,

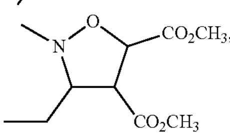, 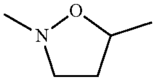,

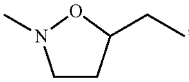, 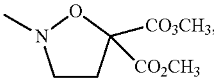,

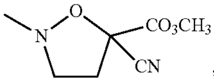, 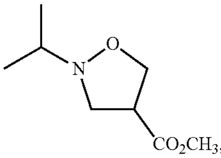,

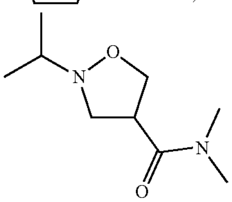, 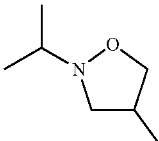,

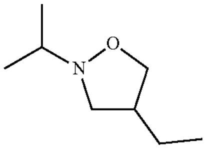, 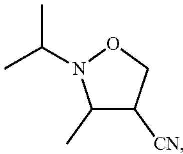,

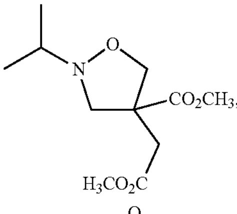, 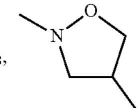, 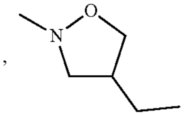,

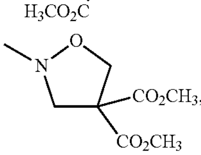 or 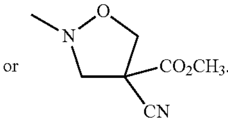.

In some embodiments, the compound of Formula III may be one of the following compounds:

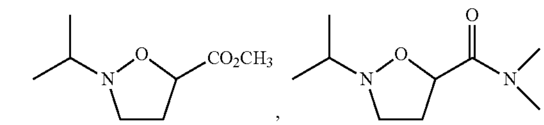

-continued

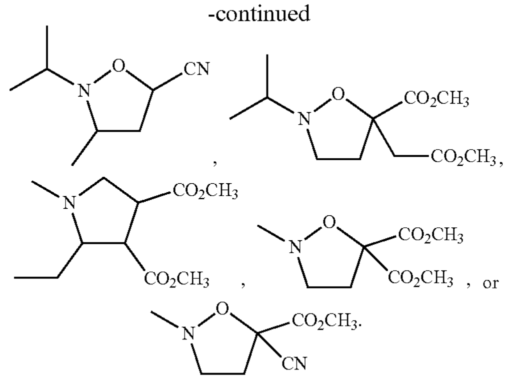

In certain embodiments, the compound is a compound of Formula IV. In some embodiments, $R^{27}$ and $R^{28}$ may each independently be —H or —Z—$NR^{35}R^{36}$. In some embodiments, $R^{27}$ may be —H and $R^{28}$ may be —Z—$NR^{35}R^{36}$. In some embodiments, $R^{28}$ may be —Z—$NR^{35}R^{36}$. In some embodiments, Z may be $C_1$—C alkylene. In some embodiments, Z may be $C_1$-$C_4$ alkylene. In some embodiments, $R^{28}$ may be —$CH(CH_3)NH_2$, —$CH(CH_3)CH_2NH_2$, —$C(CH_3)_2NH_2$, —$C(CH_3)_2CH_2NH_2$, —$CH_2NH_2$, —$N(CH_3)_2$, or —$N(CH_2CH_3)_2$. In some embodiments, $R^{28}$ may be —$C(CH_3)_2NH_2$.

In some embodiments, $R^{35}$ and $R^{36}$ may each independently be —H, —$C_1$-$C_6$ alkyl, —$C_1$-$C_6$ alkylene-OH, —$C_1$-$C_6$ alkylene-$NH_2$, —$C_1$-$C_6$ alkylene-NH—$C_1$-$C_6$ alkyl, or —$C_1$-$C_6$ alkylene-N—($C_1$-$C_6$ alkyl)$_2$. In some embodiments, $R^{35}$ and $R^{36}$ may each independently be —H, —$C_1$-$C_2$ alkyl, —$C_1$-$C_2$ alkylene-OH, —$C_1$-$C_2$ alkylene-$NH_2$, —$C_1$-$C_2$ alkylene-NH—$C_1$-$C_2$ alkyl, or —$C_1$-$C_2$ alkylene-N—($C_1$-$C_2$ alkyl)$_2$. In some embodiments, $R^{35}$ and $R^{36}$ may each independently be —H or —$C_1$-$C_2$ alkyl. In some embodiments, $R^{35}$ and $R^{36}$ may be the same. In some embodiments, $R^{35}$ and $R^{36}$ may be different.

In some embodiments, p may be 0 and $R^{29}$ and $R^{31}$ may be absent.

In some embodiments, $R^{31}$ and $R^{32}$ may each independently be —H, —$C(O)_2H$, —$CO_2CH_3$, —$C(O)N(CH_3)_2$, —$C(O)N(CH_2CH_3)_2$, —$CH_2C(O)NH_2$, —$CH_2C(O)N(CH_3)_2$, or —$CH_2C(O)N(CH_2CH_3)_2$. In some embodiments, $R^{31}$ and $R^{32}$ may be —H.

In any embodiment, the compound may be a low volatile organic compound (low VOC).

In any embodiment, the compound of Formula I, II, III, or IV has a boiling point above about 225° C. In any embodiment, the compound has a boiling point of at least about 250° C. In any embodiment, the compound has a boiling point of at least about 260° C. In any embodiment, the compound has a boiling point of at least about 270° C. In any embodiment, the compound has a boiling point of at least about 280° C.

In any embodiment, the compound of Formula I, II, III, or IV has a longer gas chromatography retention time than diethyl adipate. In any embodiment, the gas chromatography (GC) retention time may be measured according to GB 18582 test methods. In any embodiment, the gas chromatography retention time may be measured using a polydimethylsiloxane capillary column (30 m×0.32 mm×1.0 μm) with a 45° C. initial temperature, a 260° C. inlet temperature, a 280° C. detector temperature, and a 230° C. detector temperature. In any embodiment, the initial temperature may be held for 4 minutes followed by a 8° C. increase per minute. In any embodiment, the GC retention time of the compound may be at least about 0.5 second longer than diethyl adipate. In any embodiment, the GC retention time of the compound may be at least about 1.0 second longer than diethyl adipate. In any embodiment, the compound has a longer GC retention time than hexadecane. In any embodiment, the GC retention time of the compound may be at least about 0.5 second longer than hexadecane. In any embodiment, the GC retention time of the compound may be at least about 1.0 second longer than hexadecane. In any embodiment, the compound has a longer GC retention time than methyl palmitate. In any embodiment, the GC retention time of the compound may be at least about 0.5 second longer than methyl palmitate. In any embodiment, the GC retention time of the compound may be at least about 1.0 second longer than methyl palmitate.

In any embodiment, the compound has a toxicity lower than N-methyl-2-pyrrolidione. Not wishing to be bound by theory, it is speculated NMP toxicity occurs, at least in part, by oxidation at the C5 position of the pyrrolidinone ring that occurs in the body (Scheme 1). It is speculated by the present technology blocking oxidation at C5 will prevent toxicity or at least lower toxicity compared to NMP.

Scheme 1

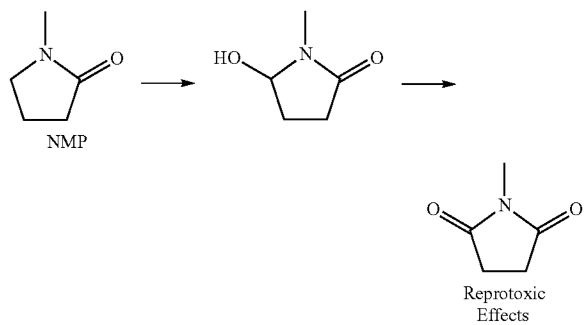

In another aspect, the present technology provides compositions that include a compound of Formula I, Formula II, Formula III, Formula IV, or a combination of two or more thereof in any embodiment disclosed herein. In any embodiment, the composition may be substantially free of NMP. In any embodiment, the composition is a known composition to contain NMP and the compound replaces the NMP in the composition. In any embodiment, the compound replaces NMP on a 1 to 1 basis (e.g., every mole of NMP is replaced with the name number of moles of the compound).

In any embodiment, the composition may be substantially free of methylene chloride. In any embodiment, the compound replaces methylene chloride in the composition. In any embodiment, the compound replaces NMP and methylene chloride in the composition.

In any embodiment, the composition may be a paint or coating, stripper (e.g., paint, photoresist, furniture, graffiti, wheel, nail polish remover), cleaner (e.g., oven, surface, floor, automotive, industrial, optic, printed circuit board, or semiconductor), adhesive/binder/sealant, leather treatment, personal care (i.e., commonly used as a surfactant), screen printing (e.g., lithographic, silk), pharmaceutical formulation, and/or manufacturing (e.g., electronic such as printed circuit board, defluxing, or semiconductor; pharmaceutical; agrochemical; petrochemicals; plasticizer; ink). In any embodiment, the composition may be any composition known for including NMP. Nonlimiting examples include those provided in "Preliminary Information on Manufacturing, Processing, Distribution, Use, and Disposal: N-Methylpyrrolidone (NMP)," Office of Chemical Safety and Pollution Prevention U.S. EPA (February 2017), which is incorporated herein by reference.

In any embodiment, the composition may be a paint or coating. In some embodiments, the composition may further include binders, pigments and/or dyes, carriers (e.g., water), dispersants, or a combination of two or more thereof.

A wide range of pigments and dyes known to those of skill in the art may be used, including blacks, blues, reds, greens, yellows, and mixtures thereof. A brief listing of some exemplary pigments and dyes may include carbon black, phthalocyanine blue, perylene black, azo dyes including metalized azo dyes, carbocyclic azo dyes and heterocyclic azo dyes, polymethine dyes, quinophthalones, sulfur dyes, nitro and nitroso dyes, cyanines, diazacarbocyanine, anthraquinone, other pigments, etc.

In any embodiment, the composition may be stripper (e.g., paint, photoresist, furniture, graffiti, wheel, nail polish remover). In some embodiments, the compound in the composition may be as an active solvent. In some embodiments, the composition may further include a second active solvent such as an alcohol, water, an amine (e.g., monoethanolamine), acid (e.g., hypophosphorous acid and/or glycolic acid), base (e.g., sodium hydroxide and/or calcium hydroxide), salt (e.g., trisodiumphosphate), peroxide, dichloroethylene, ether (e.g., aromatic ethers), surfactant, corrosion inhibitor, wax, thickener, or a combination of two or more thereof. In some embodiments, the alcohol may be phenol and/or a $C_1$-$C_6$ alcohol including a $C_1$-$C_4$ alcohol such as propanol, isopropanol, and butanol.

In any embodiment, the composition may be a cleaner (e.g., oven, surface, floor, automotive, industrial, optic, printed circuit board, or semiconductor). In some embodiments, the composition may further include water, base (e.g., sodium hydroxide, lithium, and/or calcium hydroxide), surfactant (e.g., nonionic surfactant such as tridecyloxy polyethyleneoxy ethanol and alkylphenoxy polyethoxy ethanol), thickener (e.g., colloidal magnesium aluminum silicate, such as available under the trademark Veegum T from Vanderbilt Co., alginates, ethylene oxide polymers, carboxymethyl cellulose, carboxyethyl cellulose, bentonite, and/or starches), humectant (e.g., glycerol, propylene glycol, and polyethylene glycol, and/or ethanol amines such as triethanolamine, diethanolamine, and/or monoethanolamine), organic solvent (e.g., ethylene glycol monophenyl ether, methoxy polyethylene glycol, tripropylene glycol methyl ether, diethylene glycol monophenyl ether, diethylene glycol monobutyl ether, phenylglycol ethers, and/or ethanol), alkali metal carbonate and/or bicarbonate salts, metal chelating agent, ammonium fluoride, or a combination of two or more thereof.

In any embodiment, the composition may be adhesive/binder/sealant. In some embodiments, the composition may further include resins/polymers, organic solvent (e.g., THF, MEK, $C_1$-$C_6$ alcohol, acetone, methylacetate, and the like), water, pigment and/or dye, fillers, thixotropic agents, plasticizer, lime, cement, gypsum, liquid glass, carbohydrate (e.g., cellulose and derivatives thereof, starch, and the like), wax, linseed oil, gum arabic, gums, casein, or a combination of two or more thereof.

In any embodiment, the composition may be leather treatment. In some embodiments, the composition may further include an organic solvent (e.g., naphtha and/or turpentine), oil (e.g., bovine tallow and/or mink), wax, pigment and/or dye, or a combination of two or more thereof.

In any embodiment, the composition may be personal care (i.e., commonly used as a surfactant). In some embodiments, the composition may further include water, alpha-hydroxy acids, polyhydroxy acids, hydroquinone, retinol, kojic acid, copper peptide, vitamins, minerals, moisturizers, emollients, humectants, lubricating agents, sensates, fragrances, anti-dandruff agents, buffering agents, bulking agents, chelating agents, colorants, astringents, cosmetic biocides, denaturants, anti-inflammatory agents, sunscreen agents, film formers, polymers, pH adjusters, propellants, reducing agents, sequestrants, conditioning agents, thickeners, detersive agents, or a combination of two or more thereof.

In any embodiment, the composition may be a screen printing composition (e.g., lithographic, silk). In some embodiments, the composition may further include binders, pigments and/or dyes, carriers (e.g., water, organic solvent such as $C_1$-$C_6$ alcohol, dichloropropane, toluene, acetone, xylene and derivatives thereof)), dispersants, or a combination of two or more thereof.

In any embodiment, the composition may be pharmaceutical formulation. In some embodiments, the composition may further include a pharmaceutical acceptable carrier (e.g., water), an active drug, preservative, or a combination of two or more thereof.

In any embodiment, the compositions described herein may be used for manufacturing (e.g., electronic such as printed circuit board, defluxing, or semiconductor; pharmaceutical; agrochemical; petrochemicals; plasticizer; ink).

In any embodiment, the composition may be any composition in need of acid neutralization. In any embodiment, the composition may be any composition in need of a pH increase. In some embodiments, the composition may have a pH between about 8 and 10.

In any embodiment, the composition may not be an electrolyte composition. In any embodiment, the compound may not be an electrolyte in the composition. In any embodiment, the composition may not be a microwave dielectric heating medium. In any embodiment, the composition may not be a contact lens or a precursor thereof.

In another aspect, the present technology provides methods for making the compounds of Formulas I, II, III, and IV. $R^1$-$R^{36}$, X, Z, m, n, and p are as defined herein.

In any embodiment, the method of making the compound of Formula I may include reacting a nitroalkane and an acrylate reagent to form a nitro alkanoyl reagent; optionally derivatizing the nitro alkanoyl reagent; reducing the nitro alkanoyl reagent to form an amino alkanoyl reagent; optionally derivatizing the amino alkanoyl reagent; cyclizing the amino alkanoyl reagent to form a compound of Formula Ia:

Formula Ia

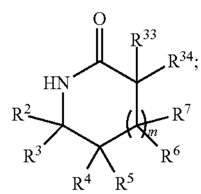

and alkylating the compound of Formula Ia to form the compound of Formula I.

In any embodiment, the nitroalkane may be compound of Formula Ib:

Formula Ib

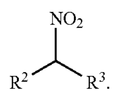

In any embodiment, the acrylate reagent may be compound of Formula IC:

Formula Ic

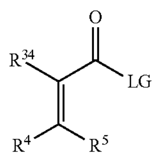

wherein LG may be any known leaving group including those described herein.

In another embodiment, the method of making the compound of Formula I may include reacting a nitroalkane and a ketone or aldehyde to form a nitroalcohol; optionally derivatizing the nitroalcohol; reducing the nitroalcohol to form an aminoalcohol; optionally derivatizing the aminoalcohol; and cyclizing the aminoalcohol in the presence of carbon dioxide to form a compound of Formula Id:

Formula Id

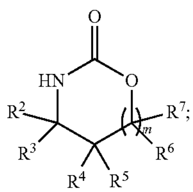

and alkylating the compound of Formula Id to form the compound of Formula I.

In any embodiment, the nitroalkane may be compound of Formula Ib:

Formula Ib

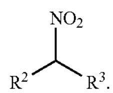

In any embodiment, the ketone or the aldehyde may be compound of Formula Ie:

Formula Ie

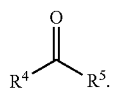

In any embodiment, the method of making the compound of Formula II may include reacting a nitroalkane and an acrylate reagent to form a nitro alkanoyl reagent; optionally derivatizing the nitro alkanoyl reagent; reducing the nitro alkanoyl reagent to form a compound of Formula IIa:

Formula IIa

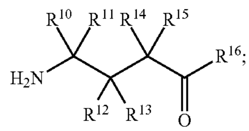

and alkylating the compound of Formula IIa to form a compound of Formula II.

In any embodiment, the nitroalkane may be compound of Formula IIb:

Formula IIb

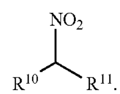

In any embodiment, the acrylate reagent may be compound of Formula IIc:

Formula IIc

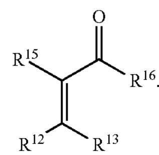

In any embodiment, the method of making the compound of Formula III may include reducing a nitroalkane to form an alkylhydroxylamine; reacting the alkylhydroxylamine and an aldehyde to form a nitrone; and reacting the nitrone and an alkene to form the compound of Formula III.

In any embodiment, the nitroalkane may be a compound of Formula IIIb:

Formula IIIb

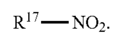

In any embodiment, the nitrone may be compound of Formula IIIc:

Formula IIIc

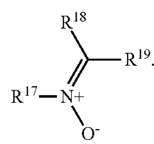

In any embodiment, the alkene may be compound of Formula IIId:

Formula IIId

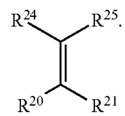

In any embodiment, the method of making the compound of Formula IV may include reacting a nitroalkane and a maleimide to form a nitropyrrolidine-dione; and reducing the nitropyrrolidine-dione to form the compound of Formula IV.

In any embodiment, the nitropyrrolidine-dione may be compound of Formula IVb:

Formula IVb

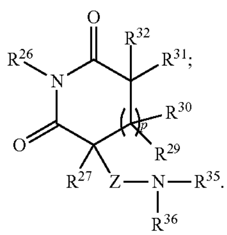

In any embodiment, one or more steps recited in any method herein may occur in a single pot. In any embodiment, two or more steps recited in any method herein may occur in a single pot. In any embodiment, three or more steps recited in any method herein may occur in a single pot.

In some embodiments, intermediate products made in any method herein may be used in the next step without purification. In other embodiments, intermediate products made in any method herein may be purified prior to being used in the next step. In any embodiment, one or more intermediate products and/or the final product may be purified by known techniques including filtration, centfrugation, chromatography, evaporation, liquid-liquid extraction, distillation (e.g., vacuum distillation), sublimation, crystallization, or a combination of two or more thereof. In any embodiment, the purifying may include distillation.

The examples herein are provided to illustrate advantages of the present technology and to further assist a person of ordinary skill in the art with preparing or using the compounds of the present technology or salts, racemic mixtures or tautomeric forms thereof. The examples herein are also presented in order to more fully illustrate the preferred aspects of the present technology. The examples should in no way be construed as limiting the scope of the present technology, as defined by the appended claims. The examples can include or incorporate any of the variations, aspects or aspects of the present technology described above. The variations, aspects or aspects described above may also further each include or incorporate the variations of any or all other variations, aspects or aspects of the present technology.

EXAMPLES

Example 1: Synthesis of a Compound of Formula I when X is Carbon

As provided in Scheme 2, methacrylate (an acrylate reagent) and 2-nitropropane (a nitroalkane) were reacted in the presence of a base followed by hydrogenation to produce methyl-4-amino-4-methylpentanoate (an amino alkanoyl reagent). Methyl-4-amino-4-methylpentanoate was then cyclized to form 5,5-dimethylpyrrolidin-2-one (a compound of Formula Ia) followed by methylation to produce 1,5,5-trimethylpyrrolidin-2-one.

In particular, a 2-liter multi-neck round bottom flask was fitted with a reflux condenser and addition funnel. The flask was charged with 5.0 g (0.043 mol) of 1,1,3,3-tetramethylguanidine (TMG, 99%, Aldrich). To the addition funnel a blend of 405 g (4.55 mol) of 2-nitropropane (2NP, 98+%, ANGUS Chemical Co.) and 383 g (4.45 mol) of methyl acrylate (MA, 99%, contains ≤100 ppm monomethyl ether hydroquinone as inhibitor, Aldrich) was charged. Under stirring, the blend of 2NP/MA was added in portions to the flask. The exothermic reaction was allowed to heat the reactor contents to 110° C. The blend of 2NP/DMAA was added to the flask at a rate to maintain 105-110° C. After complete addition of the blend of 2NP/MA, the mixture was stirred for 30 minutes at 110° C. GC analysis indicated >99% conversion of MA to a cyan liquid nitro ester.

100 g water, 200 g methanol, and 30 g of damp Raney® nickel were added to a 2 L Parr reactor. The reactor was purged with hydrogen. Under stirring, the nitro ester resulting from the previous reaction was added to the reactor while maintain a temperature of 65° C. Following complete addition of the nitro ester, the reagents were stirred and reacted at 65° C. for 30 minutes followed by cooling to 25° C. The reactor was vented and the catalyst filtered off the product. After rinsing the catalyst with 250 g water, the filtrate was concentrated by heating to 150° C. under atmospheric pressure. Once the temperature reached 150° C., vacuum was applied to 150 mmHg. The temperature and vacuum were held for 1 hour until condensate ceased to form and the reaction mixture was completely liquefied. The product was isolated and purified using vacuum distillation to provide a product that solidified on standing at room temperature. The isolated yield was 425 g (84.4% yield from methyl acrylate) of a colorless solid. $^1$H NMR ($D_2O$) was consistent with the assigned structure. The purity was 99.5% by GC-FID.

To a 1-liter round bottom flask 210 g (1.86 mol) of 5,5-dimethyl-2-pyrrolidinone and 210 g (2.59 mol) of formaldehyde (Fisher Scientific, 37% aqueous) were added, followed by addition of 2.1 g of sodium hydroxide (50% aqueous). The mixture was stirred at ambient temperature for 16 hours. The reaction mixture was dealkalinized using ion exchange chromatography: Dowex MAC-3 H-form, 60×2 cm column (120 mL bed volume, washed with 4-6 BV water) at 10 mL/min flow rate. The eluate was neutral to pH strips. The product was concentrated at 100° C. and 20 mmHg for 1 hour to provide 255 g of a pale yellow liquid. The isolated yield was 96.0%. The product was ≥98% pure by GC-FID. $^1$H NMR (400 MHz, $D_2O$): δ=4.66 (s, 2H), 2.36 (t, 2H), 1.83 (t, 2H), 1.21 (s, 6H).

Hydrogenolysis of 1-(hydroxymethyl)-5,5-dimethylpyrrolidin-2-one (performed according to J. Auerbach, M. Zamore, and S. M. Weinreb, J. Org. Chem. 1976, 41 (4), 725-726) to produce 1,5,5-trimethylpyrrolidin-2-one in 48% yield as determined by GC-FID analysis.

Scheme 2

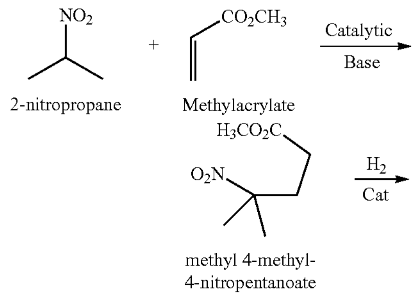

2-nitropropane

Methylacrylate methyl 4-methyl-4-nitropentanoate

-continued

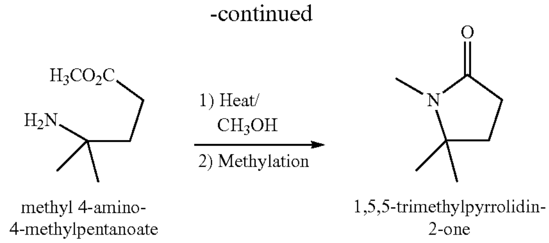

methyl 4-amino-4-methylpentanoate 1,5,5-trimethylpyrrolidin-2-one

Example 2: Synthesis of a Compound of Formula I when X is Oxygen

As provided in Scheme 3, formaldehyde and 2-nitropropane were reacted followed by hydrogenation to produce 2-amino-2-methylpropan-1-ol (an aminoalcohol). 2-amino-2-methylpropan-1-ol was then reacted with carbon dioxide to produce 4,4-dimethyloxazolidin-2-one (a compound of Formula Id). 4,4-dimethyloxazolidin-2-one was then methylated to produce 3,4,4-trimethyloxazolidin-2-one.

Scheme 3

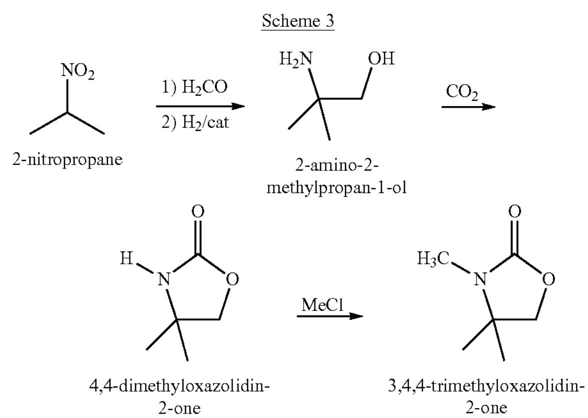

2-nitropropane 2-amino-2-methylpropan-1-ol 4,4-dimethyloxazolidin-2-one 3,4,4-trimethyloxazolidin-2-one Example 3: Synthesis of a Compound of Formula II As provided in Scheme 4, N,N-dimethylacrylamide (an acrylate reagent) and 2-nitropropane (a nitroalkane) were reacted in the presence of a base to produce N,N-4-trimethyl-4-nitropentamide (a nitro alkanoyl reagent). N,N-4-trimethyl-4-nitropentamide was then hydrogenated to form 4-amino-N,N,4-trimethylpentanamide (a compound of Formula IIa) and methylated to produce 4-(dimethylamino)-N,N-4-trimethylpentamide.

In particular, a 2-liter multi-neck round bottom flask was fit with a reflux condenser and addition funnel. The flask was charged with 8.75 g (0.76 mol) of 1,1,3,3-tetramethylguanidine (TMG, 99%, Aldrich). To the addition funnel charge a blend of 425 g (4.77 mol) of 2-nitropropane (2NP, 98+%, ANGUS Chemical Co.) and 450 g (4.54 mol) of N,N-dimethylacrylamide (DMAA, 99%, contains 500 ppm monomethyl ether hydroquinone as inhibitor, Aldrich) was added. Under stirring, the blend of 2NP/DMAA was added in portions to the flask. The exothermic reaction was allowed to heat the reactor contents to 75° C. The blend of 2NP/DMAA was added to the flask at a rate to maintain 70-80° C. After complete addition of the blend of 2NP/DMAA, the mixture was stirred for 8 hours at 75° C. GC analysis indicated 98% conversion of DMAA to provide a yellow liquid nitro amide.

The resulting nitro amidef was added to a 2 L Parr reactor along with 300 g methanol and 30 g of damp Raney® nickel. The reactor was purged with hydrogen. The reagents were stirred and reacted at 65° C. and 750 psig hydrogen. In a separate vessel, a blend of 400 g (2.13 mol) of nitroamide (prepared in previous example) and 431 g (5.31 mol) of formaldehyde (37% aqueous, Fisher Scientific) was prepared. The nitroamide/formaldehyde mixture was added to the reactor under stirring while maintaining 65° C. Followed by flushing with 50 g (0.62 mol) of 37% aqueous formaldehyde. The reactor contents were held at 65° C. for 2 hours followed by cooling to 25° C. The reactor was vented and the catalyst filtered off the product. After rinsing the catalyst with methanol (2×20 mL), the filtrate was concentrate under vacuum. The product was isolated and purified using vacuum distillation to provide a pale yellow liquid recovered in 75% yield from DMAA having purity >99% by GC-FID. The boiling point was determined to be 170° C. at 40 mmHg, 145° C. at 15 mmHg, and 137° C. at 10 mmHg. $^1$H NMR (400 MHz, $D_2O$): d=2.95 (s, 3H), 2.88 (s, 3H), 2.24 (m, 2H), 2.05 (s, 6H), 1.54 (m, 2H), 0.91 (s, 6H). The product was soluble in water and mineral oil and at dissolved lithium grease, beeswax, asphalt, and dried styrene acrylic paint better than NMP.

Scheme 4

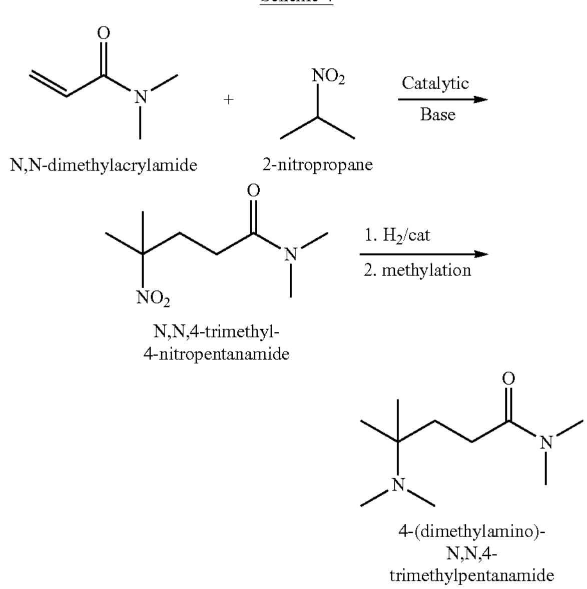

N,N-dimethylacrylamide 2-nitropropane

N,N,4-trimethyl-4-nitropentanamide 4-(dimethylamino)-N,N,4-trimethylpentanamide

Example 4: Synthesis of a Compound of Formula III

As provided in Scheme 5, 2-nitropropane (a nitroalkane) was reduced to produce N-isopropylhydroxylamine (an alkylhydroxylamine). N-isopropylhydroxylamine was reacted with formaldehyde to form N-isopropylmethanimine oxide (a nitrone) followed by a reaction with methyl acrylate (an alkene) to produce methyl 2-isopropylisoxazolidine-5-carboxylate.

Scheme 5

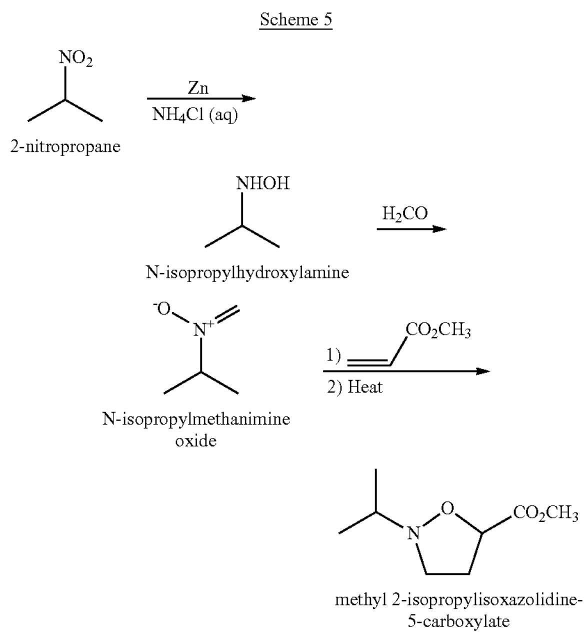

2-nitropropane

N-isopropylhydroxylamine

N-isopropylmethanimine oxide methyl 2-isopropylisoxazolidine-5-carboxylate

Example 5: Synthesis of a Compound of Formula IV

As provided in Scheme 6, maleimide and 2-nitropropane (a nitroalkane) were reacted in the presence of a base to produce 3-(2-nitropropan-2-yl)pyrrolidine-2,5-dione (a nitropyrrolidine-dione). 3-(2-nitropropan-2-yl)pyrrolidine-2,5-dione was then hydrogenated to produce 3-(2-amino-propan-2-yl)pyrrolidine-2,5-dione.

Scheme 6

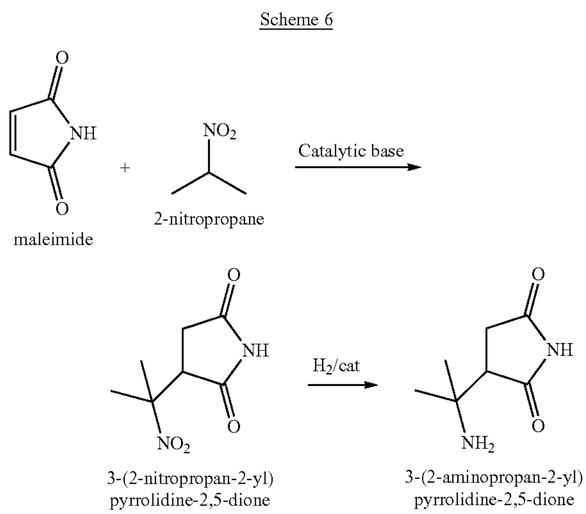

maleimide 2-nitropropane 3-(2-nitropropan-2-yl) pyrrolidine-2,5-dione 3-(2-aminopropan-2-yl) pyrrolidine-2,5-dione

ILLUSTRATIVE EMBODIMENTS

Paragraph 1. A compound of Formula I, Formula II, Formula III, or Formula IV:

Formula I

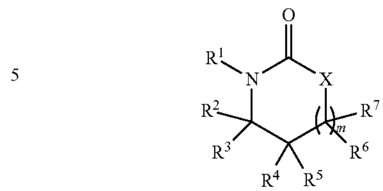

Formula II

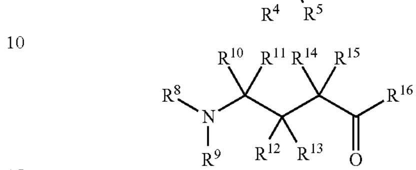

Formula III

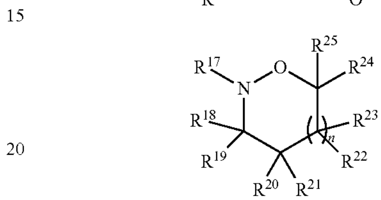

Formula IV

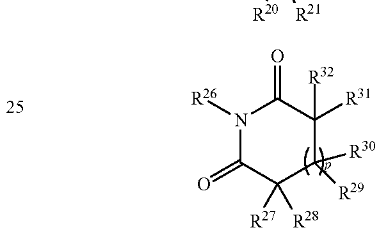

wherein: X is O or $CR^{33}R^{34}$; $R^1$, $R^8$, $R^9$, $R^{17}$, and $R^{26}$ are each independently $—CH_3$, $—CH_2CH_3$, $—CH_2CH_2CH_3$, or $—CH(CH_3)_2$; $R^2$, $R^3$, $R^{10}$, $R^{11}$, $R^{14}$, and $R^{15}$ are each independently —H, $—CH_3$, or $—CH_2CH_3$; $R^6$ and $R^7$ are each independently absent, —H, $—CH_3$, $—CH_2CH_3$, —CN, $—C(O)N(CH_3)_2$, $—CH_2C(O)N(CH_3)_2$, $—C(O)N(CH_2CH_3)_2$, $—CH_2C(O)N(CH_2CH_3)_2$, $—CO_2CH_3$, or $—CH_2CO_2CH_3$; $R^{16}$ is $—O—C_1$-$C_8$ alkyl, $—O—C_2$-$C_8$ (hetero)cycloalkyl, $—O—C_4$-$C_{12}$ (hetero)aryl, $—NH_2$, $—NH—C_1$-$C_8$ alkyl, $—N(C_1$-$C_8$ alkyl$)_2$,

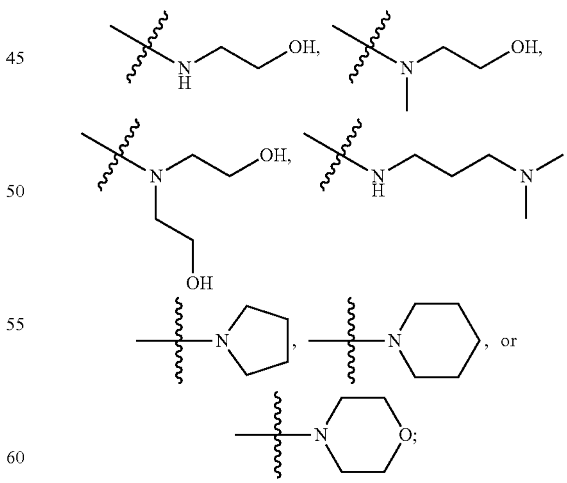

, or $R^{18}$ and $R^{19}$ are each independently —H or $—C_1$-$C_8$ alkyl; $R^{22}$ and $R^{23}$ are each independently absent, —H or $—C_1$-$C_8$ alkyl; $R^{24}$ and $R^{25}$ are each independently —H, —CN, $—C_1$-$C_8$ alkyl, $—C_2$-$C_8$ (hetero)cycloalkyl, $—CH_2—O—C_1$-$C_8$ alkyl, $—C(O)—C_1$-$C_8$ alkyl, $—C_1$-$C_8$ alkylene-C (O)—$C_1$-$C_8$ alkyl, —C(O)—$C_2$-$C_8$ (hetero)cycloalkyl, —$C_1$-$C_8$ alkylene-C(O)—$C_2$-$C_8$ (hetero)cycloalkyl, —$CO_2H$, —$CO_2$—$C_1$-$C_8$ alkyl, —$C_1$-$C_8$ alkylene-$CO_2$—$C_1$-$C_8$ alkyl, —$CO_2$—$C_2$-$C_8$ (hetero)cycloalkyl, —$C_1$-$C_8$ alkylene-$CO_2$—$C_2$-$C_8$ (hetero)cycloalkyl, —$C_1$-$C_8$ alkylene-$NH_2$, —$C_1$-$C_8$ alkylene-NH—$C_1$-$C_8$ alkyl, —$C_1$-$C_8$ alkylene-N($C_1$-$C_8$ alkyl)$_2$, —C(O)$NH_2$, —$C_1$-$C_8$ alkylene-C(O)$NH_2$, —C(O)NH—$C_1$-$C_8$ alkyl, —C(O)N($C_1$-$C_8$ alkyl)$_2$, —$C_1$-$C_8$ alkylene-C(O)NH—$C_1$-$C_8$ alkyl, —$C_1$-$C_8$ alkylene-C(O)N($C_1$-$C_8$ alkyl)$_2$, -(hetero)aryl, -(hetero)cycloalkyl,

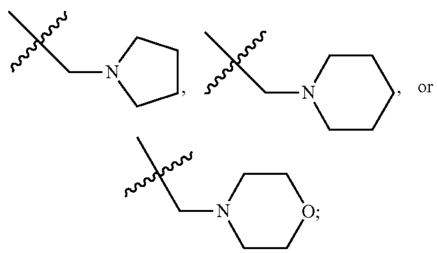

$R^4$, $R^5$, $R^{12}$, $R^{13}$, $R^{20}$, $R^{21}$, $R^{31}$, $R^{32}$, $R^{33}$, and $R^{34}$ are each independently —H, —CN, —$C_1$-$C_8$ alkyl, —$C_2$-$C_8$ (hetero)cycloalkyl, —O—$C_1$-$C_8$ alkyl, —$CH_2$—O—$C_1$-$C_8$ alkyl, —C(O)—$C_1$-$C_8$ alkyl, —$C_1$-$C_8$ alkylene-C(O)—$C_1$-$C_8$ alkyl, —C(O)—$C_3$-$C_8$ cycloalkyl, —$C_1$-$C_8$ alkylene-C(O)—$C_2$-$C_8$ (hetero)cycloalkyl, —$CO_2H$, —$CO_2$—$C_1$-$C_8$ alkyl, —$C_1$-$C_8$ alkylene-$CO_2$—$C_1$-$C_8$ alkyl, —$CO_2$—$C_2$-$C_8$ (hetero)cycloalkyl, —$C_1$-$C_8$ alkylene-$CO_2$—$C_2$-$C_8$ (hetero)cycloalkyl, —$NH_2$, —$C_1$-$C_8$ alkylene-$NH_2$, —NH—$C_1$-$C_8$ alkyl, —N($C_1$-$C_8$ alkyl)$_2$, —$C_1$-$C_8$ alkylene-NH—$C_1$-$C_8$ alkyl, —$C_1$-$C_8$ alkylene-N($C_1$-$C_8$ alkyl)$_2$, —C(O)$NH_2$, —$C_1$-$C_8$ alkylene-C(O)$NH_2$, —C(O)NH—$C_1$-$C_8$ alkyl, —C(O)N($C_1$-$C_8$ alkyl)$_2$, —$C_1$-$C_8$ alkylene-C(O)NH—$C_1$-$C_8$ alkyl, —$C_1$-$C_8$ alkylene-C(O)N($C_1$-$C_8$ alkyl)$_2$, -(hetero)aryl, -(hetero)cycloalkyl,

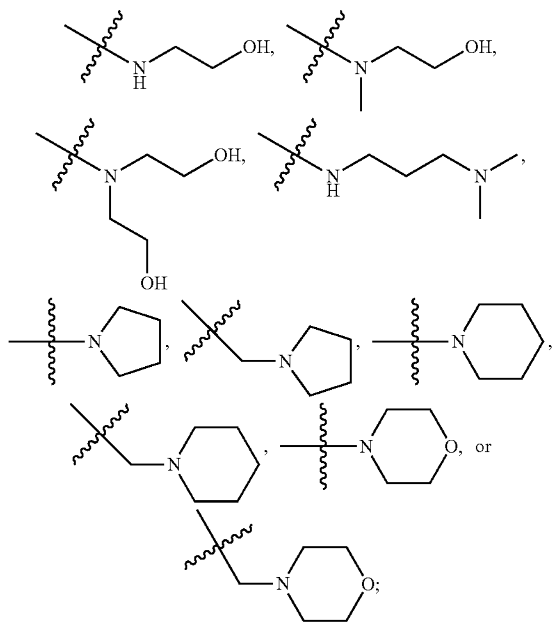

$R^{27}$ and $R^{28}$ are each independently —H or —Z—$NR^{35}R^{36}$, wherein: Z is a $C_1$-$C_8$ alkylene; and $R^{35}$ and $R^{36}$ are each independently —H, —$C_1$-$C_8$ alkyl, -(hetero)aryl, -(hetero)cycloalkyl, —$C_1$-$C_8$ alkylene-OH, —$C_1$-$C_8$ alkylene-$NH_2$, —$C_1$-$C_8$ alkylene-NH—$C_1$-$C_8$ alkyl, or —$C_1$-$C_8$ alkylene-N—($C_1$-$C_8$ alkyl)$_2$; $R^{29}$ and $R^{30}$ are each independently absent, —H, —$CH_3$, or —$CH_2CH_3$; and m, n, and p are each independently 0 or 1.

Paragraph 2. The compound of paragraph 1, wherein $R^1$ is —$CH_3$.

Paragraph 3. The compound of paragraph 1, wherein $R^1$ is —$CH_2CH_3$.

Paragraph 4. The compound of paragraph 1, wherein $R^1$ is —$CH_2CH_2CH_3$ or —$CH(CH_3)_2$.

Paragraph 5. The compound of any one of paragraphs 1-4, wherein $R^8$ is —$CH_3$.

Paragraph 6. The compound of any one of paragraphs 1-4, wherein $R^8$ is —$CH_2CH_3$.

Paragraph 7. The compound of any one of paragraphs 1-4, wherein $R^8$ is —$CH_2CH_2CH_3$ or —$CH(CH_3)_2$.

Paragraph 8. The compound of any one of paragraphs 1-7, wherein $R^9$ is —$CH_3$.

Paragraph 9. The compound of any one of paragraphs 1-7, wherein $R^9$ is —$CH_2CH_3$.

Paragraph 10. The compound of any one of paragraphs 1-7, wherein $R^9$ is —$CH_2CH_2CH_3$ or —$CH(CH_3)_2$.

Paragraph 11. The compound of any one of paragraphs 1-10, wherein $R^{17}$ is —$CH_3$.

Paragraph 12. The compound of any one of paragraphs 1-10, wherein $R^{17}$ is —$CH_2CH_3$.

Paragraph 13. The compound of any one of paragraphs 1-10, wherein $R^{17}$ is —$CH_2CH_2CH_3$ or —$CH(CH_3)_2$.

Paragraph 14. The compound of any one of paragraphs 1-13, wherein $R^{26}$ is —$CH_3$.

Paragraph 15. The compound of any one of paragraphs 1-13, wherein $R^{26}$ is —$CH_2CH_3$.

Paragraph 16. The compound of any one of paragraphs 1-13, wherein $R^{26}$ is —$CH_2CH_2CH_3$ or —$CH(CH_3)_2$.

Paragraph 17. The compound of any one of paragraphs 1-16, wherein $R^2$ is —H.

Paragraph 18. The compound of any one of paragraphs 1-16, wherein $R^2$ is —$CH_3$.

Paragraph 19. The compound of any one of paragraphs 1-16, wherein $R^2$ is —$CH_2CH_3$.

Paragraph 20. The compound of any one of paragraphs 1-19, wherein $R^3$ is —H.

Paragraph 21. The compound of any one of paragraphs 1-19, wherein $R^3$ is —$CH_3$.

Paragraph 22. The compound of any one of paragraphs 1-19, wherein $R^3$ is —$CH_2CH_3$.

Paragraph 23. The compound of any one of paragraphs 1-22, wherein $R^{10}$ is —H.

Paragraph 24. The compound of any one of paragraphs 1-22, wherein $R^{10}$ is —$CH_3$.

Paragraph 25. The compound of any one of paragraphs 1-22, wherein $R^{10}$ is —$CH_2CH_3$.

Paragraph 26. The compound of any one of paragraphs 1-25, wherein $R^{11}$ is —H.

Paragraph 27. The compound of any one of paragraphs 1-25, wherein $R^{11}$ is —$CH_3$.

Paragraph 28. The compound of any one of paragraphs 1-25, wherein $R^{11}$ is —$CH_2CH_3$.

Paragraph 29. The compound of any one of paragraphs 1-28, wherein $R^{14}$ is —H.

Paragraph 30. The compound of any one of paragraphs 1-28, wherein $R^{14}$ is —$CH_3$.

Paragraph 31. The compound of any one of paragraphs 1-28, wherein $R^{14}$ is —$CH_2CH_3$.

Paragraph 32. The compound of any one of paragraphs 1-31, wherein $R^{15}$ is —H.

Paragraph 33. The compound of any one of paragraphs 1-31, wherein $R^{15}$ is —$CH_3$.

Paragraph 34. The compound of any one of paragraphs 1-31, wherein $R^{15}$ is —$CH_2CH_3$.

Paragraph 35. The compound of any one of paragraphs 1-34, wherein $R^6$, $R^7$, $R^{22}$, $R^{23}$, $R^{29}$, and $R^{30}$ are each absent and m, n, and p are each 0.

Paragraph 36. The compound of any one of paragraphs 1-34, wherein m, n, and p are each 1.

Paragraph 37. The compound of paragraph 36, wherein $R^6$ is —H.

Paragraph 38. The compound of paragraph 36, wherein $R^6$ is —$CH_3$.

Paragraph 39. The compound of paragraph 36, wherein $R^6$ is —$CH_2CH_3$.

Paragraph 40. The compound of paragraph 36, wherein $R^6$ is —CN, —$C(O)N(CH_3)_2$, —$CH_2C(O)N(CH_3)_2$, —$CO_2CH_3$, or —$CH_2CO_2CH_3$.

Paragraph 41. The compound of paragraph 40, wherein $R^6$ is —$CO_2CH_3$ or —$CH_2CO_2CH_3$.

Paragraph 42. The compound of paragraph 40 or paragraph 41, wherein $R^6$ is —$CO_2CH_3$.

Paragraph 43. The compound of any one of paragraphs 36-42, wherein $R^7$ is —H.

Paragraph 44. The compound of any one of paragraphs 36-42, wherein $R^7$ is —$CH_3$.

Paragraph 45. The compound of any one of paragraphs 36-42, wherein $R^7$ is —$CH_2CH_3$.

Paragraph 46. The compound of any one of paragraphs 36-42, wherein $R^7$ is —CN, —$C(O)N(CH_3)_2$, —$CH_2C(O)N(CH_3)_2$, —$CO_2CH_3$, or —$CH_2CO_2CH_3$.

Paragraph 47. The compound of paragraph 46, wherein $R^7$ is —$CO_2CH_3$ or —$CH_2CO_2CH_3$.

Paragraph 48. The compound of paragraph 46 or paragraph 47, wherein $R^7$ is —$CO_2CH_3$.

Paragraph 49. The compound of any one of paragraphs 36-48, wherein $R^{22}$ is —H.

Paragraph 50. The compound of any one of paragraphs 36-48, wherein $R^{22}$ is —$CH_3$.

Paragraph 51. The compound of any one of paragraphs 36-48, wherein $R^{22}$ is —$CH_2CH_3$.

Paragraph 52. The compound of any one of paragraphs 36-51, wherein $R^{23}$ is —H.

Paragraph 53. The compound of any one of paragraphs 36-51, wherein $R^{23}$ is —$CH_3$.

Paragraph 54. The compound of any one of paragraphs 36-51, wherein $R^{23}$ is —$CH_2CH_3$.

Paragraph 55. The compound of any one of paragraphs 36-54, wherein $R^{29}$ is —H.

Paragraph 56. The compound of any one of paragraphs 36-54, wherein $R^{29}$ is —$CH_3$.

Paragraph 57. The compound of any one of paragraphs 36-54, wherein $R^{29}$ is —$CH_2CH_3$.

Paragraph 58. The compound of any one of paragraphs 36-57, wherein $R^{30}$ is —H.

Paragraph 59. The compound of any one of paragraphs 36-57, wherein $R^{30}$ is —$CH_3$.

Paragraph 60. The compound of any one of paragraphs 36-57, wherein $R^{30}$ is —$CH_2CH_3$.

Paragraph 61. The compound of any one of paragraphs 1-60, wherein $R^4$, $R^5$, $R^{12}$, $R^{13}$, $R^{20}$, $R^{21}$, $R^{31}$, $R^{32}$, $R^{33}$, and $R^{34}$ are each independently —H, —CN, —$CH_3$, —$CH_2CH_3$, —$OCH_3$, —$OCH_2CH_3$, —$C(O)CH_3$, —$C(O)CH_2CH_3$, —$CH_2C(O)CH_3$, —$CH_2COCH_2CH_3$, —$C(O)_2H$, —$CO_2CH_3$, —$CO_2CH_2CH_3$, —$CH_2CO_2CH_3$, —$CH_2CO_2CH_2CH_3$, —$NH_2$, —$CH(CH_3)NH_2$, —$CH_2CH(CH_3)NH_2$, —$CH(CH_3)CH_2NH_2$, —$C(CH_3)_2NH_2$, —$CH_2C(CH_3)_2NH_2$, —$C(CH_3)_2CH_2NH_2$, —$CH_2NH_2$, —$CH_2CH_2NH_2$, —$CH_2CH_2CH_2NH_2$, —$N(CH_3)_2$, —$N(CH_2CH_3)_2$, —$CH_2N(CH_3)_2$, —$CH_2N(CH_2CH_3)_2$, —$C(O)N(CH_3)_2$, —$C(O)N(CH_2CH_3)_2$, —$CH_2C(O)NH_2$, —$CH_2C(O)N(CH_3)_2$, —$CH_2C(O)N(CH_2CH_3)_2$, $C_4$-$C_{12}$ (hetero)aryl, $C_2$-$C_8$ (hetero)cycloalkyl,

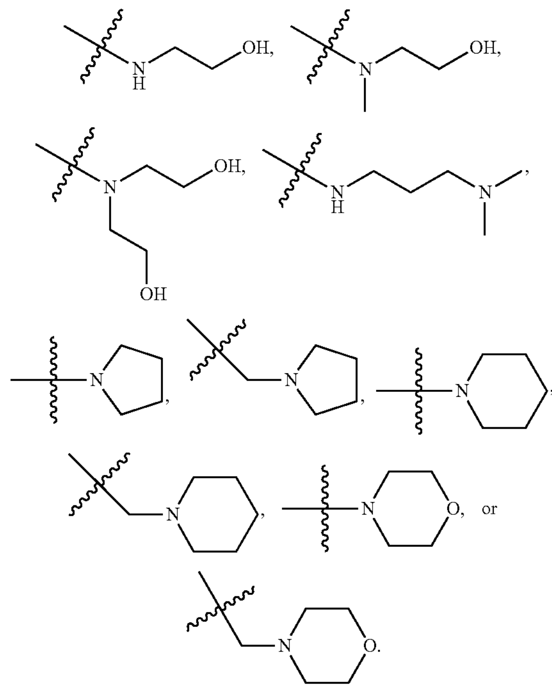

Paragraph 62. The compound of any one of paragraphs 1-61, wherein $R^4$, $R^5$, $R^{33}$, and $R^{34}$ are each independently —H, —CN, —$CH_3$, —$CH_2CH_3$, —$C(O)CH_3$, —$C(O)CH_2CH_3$, —$CH_2C(O)CH_3$, —$CH_2COCH_2CH_3$, —$CO_2H$, —$CO_2CH_3$, —$CO_2CH_2CH_3$, —$CH_2CO_2CH_3$, —$CH_2CO_2CH_2CH_3$, —$C(O)N(CH_3)_2$, —$C(O)N(CH_2CH_3)_2$, —$CH_2C(O)NH_2$, —$CH_2C(O)N(CH_3)_2$, —$CH_2C(O)N(CH_2CH_3)_2$,

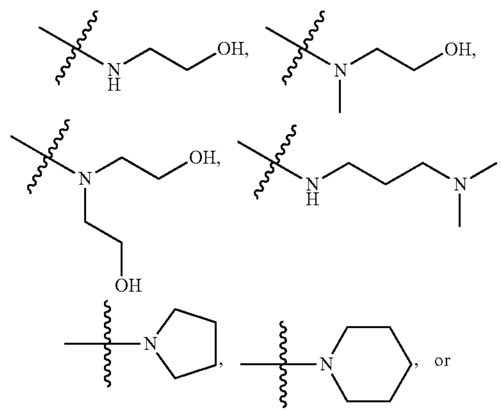

-continued

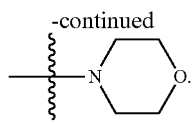

Paragraph 63. The compound of any one of paragraphs 1-62, wherein $R^4$, $R^5$, $R^{33}$, and $R^{34}$ are each independently —H, —CN, —$CH_3$, —$CH_2CH_3$, —C(O)$CH_3$, —$CH_2$C(O)$CH_3$, —$CO_2$H, —$CO_2CH_3$, —$CH_2CO_2CH_3$, or —C(O)N$(CH_3)_2$.

Paragraph 64. The compound of any one of paragraphs 1-63, wherein $R^4$ is —H.

Paragraph 65. The compound of any one of paragraphs 1-64, wherein $R^5$ is —H, —$CO_2$H, or —$CO_2CH_3$.

Paragraph 66. The compound of any one of paragraphs 1-65, wherein X is $CR^{33}R^{34}$.

Paragraph 67. The compound of paragraph 66, wherein $R^{33}$ is —H or —$CO_2CH_3$.

Paragraph 68. The compound of paragraph 66 or paragraph 67, wherein $R^{34}$ is —H, —CN, —$CH_3$, —C(O)$CH_3$, —$CO_2CH_3$, —$CH_2CO_2CH_3$, or —C(O)N$(CH_3)_2$.

Paragraph 69. The compound of any one of paragraphs 66-68, wherein at least one of $R^4$, $R^5$, $R^{33}$, and $R^{34}$ is not H.

Paragraph 70. The compound of any one of paragraphs 66-68, wherein $R^4$ is —H and least one of $R^5$, $R^{33}$, and $R^{34}$ is not —H.

Paragraph 71. The compound of any one of paragraphs 66-68, wherein $R^4$, $R^5$, $R^{33}$, and $R^{34}$ are each —H and at least one of $R^6$ and $R^7$ is not —H.

Paragraph 72. The compound of any one of paragraphs 66-68 or paragraph 71, wherein $R^6$ and $R^7$ are each independently —H, —$CH_3$, —$CH_2CH_3$, —CN, —C(O)N$(CH_3)_2$, —$CH_2$C(O)N$(CH_3)_2$, —C(O)N$(CH_2CH_3)_2$, —$CH_2$C(O)N$(CH_2CH_3)_2$, —$CO_2CH_3$, or —$CH_2CO_2CH_3$.

Paragraph 73. The compound of any one of paragraphs 66-68, 71, or 72, wherein $R^6$ is —H and $R^7$ is —CN, —C(O)N$(CH_3)_2$, —$CH_2$C(O)N$(CH_3)_2$, —C(O)N$(CH_2CH_3)_2$, —$CH_2$C(O)N$(CH_2CH_3)_2$, —$CO_2CH_3$, or —$CH_2CO_2CH_3$.

Paragraph 74. The compound of paragraph 73, wherein $R^6$ is —H and $R^7$ is —$CO_2CH_3$.

Paragraph 75. The compound of any one of paragraphs 1-65, wherein X is O.

Paragraph 76. The compound of paragraph 75, wherein $R^4$ and $R^5$ are —H.

Paragraph 77. The compound of any one of paragraphs 1-61, wherein $R^{12}$ is —H.

Paragraph 78. The compound of any one of paragraphs 1-61 or 77, wherein $R^{13}$ is —H, —$CH_3$, —$CH_2CH_3$, —CN, —C(O)N$(CH_3)_2$, —$CH_2$C(O)N$(CH_3)_2$, —C(O)N$(CH_2CH_3)_2$, —$CH_2$C(O)N$(CH_2CH_3)_2$, —$CO_2CH_3$, or —$CH_2CO_2CH_3$.

Paragraph 79. The compound of any one of paragraphs 1-61, 77, or 78, wherein $R^{13}$ is —H or —$CH_3$.

Paragraph 80. The compound of any one of paragraphs 1-61 or 77-79, wherein $R^{14}$ is —H.

Paragraph 81. The compound of any one of paragraphs 1-61 or 77-79, wherein $R^{14}$ is —$CH_3$.

Paragraph 82. The compound of any one of paragraphs 1-61 or 77-81, wherein $R^{16}$ is —$OCH_3$, —$OCH_2CH_3$, —N$(CH_3)_2$, —N$(CH_2CH_3)_2$,

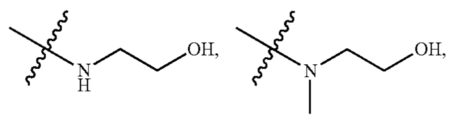

-continued

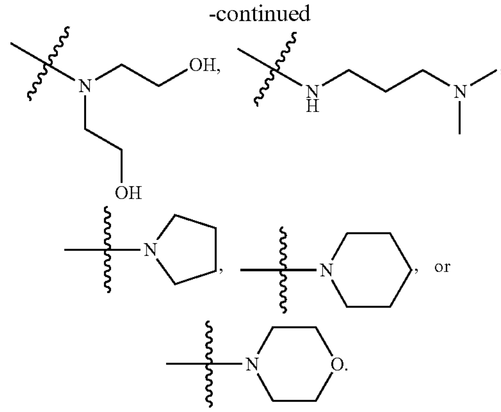

Paragraph 83. The compound of any one of paragraphs 1-61 or 77-82, wherein $R^{16}$ is —$OCH_3$, —N$(CH_3)_2$, or

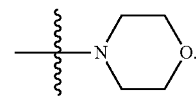 [SMILES: *N1CCOCC1]

Paragraph 84. The compound of any one of paragraphs 1-61, wherein $R^{18}$ and $R^{19}$ are each independently —H or —$C_1$-$C_6$ alkyl; $R^{20}$ and $R^{21}$ are each independently —H, —CN, —$CH_3$, —$CH_2CH_3$, —C(O)$CH_3$, —C(O)$CH_2CH_3$, —$CH_2$C(O)$CH_3$, —$CH_2COCH_2CH_3$, —C(O)$_2$H, —$CO_2CH_3$, —$CO_2CH_2CH_3$, —$CH_2CO_2CH_3$, —$CH_2CO_2CH_2CH_3$, —C(O)N$(CH_3)_2$, —C(O)N$(CH_2CH_3)_2$, —$CH_2$C(O)$NH_2$, —$CH_2$C(O)N$(CH_3)_2$, —$CH_2$C(O)N$(CH_2CH_3)_2$, —$C_4$-$C_{12}$ (hetero)aryl, —$C_2$-$C_8$ (hetero)cycloalkyl,

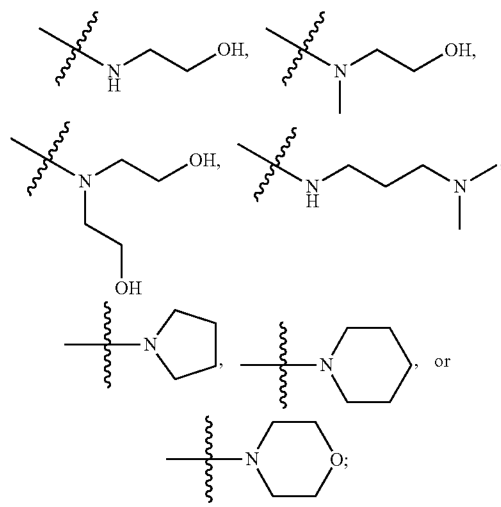

and $R^{24}$ and $R^{25}$ are each independently —H, —CN, —$C_1$-$C_4$ alkyl, —$C_2$-$C_6$ (hetero)cycloalkyl, —$CH_2$—O—$C_1$-$C_4$ alkyl, —C(O)—$C_1$-$C_4$ alkyl, —$C_1$-$C_4$ alkylene-C(O)—$C_1$-$C_4$ alkyl, —C(O)—$C_2$-$C_6$ (hetero)cycloalkyl, —$C_1$-$C_4$ alkylene-C(O)—$C_2$-$C_6$ (hetero)cycloalkyl, —$CO_2$H, —$CO_2$—$C_1$-$C_4$ alkyl, —$C_1$-$C_4$ alkylene-$CO_2$—$C_1$-$C_4$ alkyl, —$CO_2$—$C_2$-$C_6$ (hetero)cycloalkyl, —$C_1$-$C_4$ alkylene-$CO_2$—$C_2$-$C_6$ (hetero)cycloalkyl, —$C_1$-$C_4$ alkylene-$NH_2$, —$C_1$-$C_4$ alkylene-NH—$C_1$-$C_4$ alkyl, —$C_1$-$C_4$ alkylene-N($C_1$-$C_4$ alkyl)$_2$, —C(O)$NH_2$, —$C_1$-$C_4$ alkylene-C(O)$NH_2$, —C(O)NH—$C_1$-$C_4$ alkyl, —C(O)N($C_1$-$C_4$ alkyl)$_2$, —$C_1$-$C_4$ alkylene-C(O)NH—$C_1$-$C_4$ alkyl, —$C_1$-$C_4$ alkylene-C(O)N($C_1$-$C_4$ alkyl)$_2$, —$C_4$-$C_{12}$ (hetero)aryl, or —$C_3$-$C_6$ (hetero)cycloalkyl.

Paragraph 85. The compound of any one of paragraphs 1-61 or 84, wherein $R^{18}$ and $R^{19}$ are each independently —H or —$C_1$-$C_4$ alkyl; and $R^{20}$, $R^{21}$, $R^{24}$, and $R^{25}$ are each independently —H, —CN, —$CH_3$, —$CH_2CH_3$, —C(O)$CH_3$, —$CH_2$C(O)$CH_3$, —$CO_2CH_3$, —$CH_2CO_2CH_3$, —C(O)N($CH_3$)$_2$, phenyl, cyclopentyl, or cyclohexyl.

Paragraph 86. The compound of any one of paragraphs 1-61, 84, or 85, wherein $R^{18}$ is —H.

Paragraph 87. The compound of any one of paragraphs 1-61 or 84-86, wherein $R^{19}$ is —H or —$CH_3$.

Paragraph 88. The compound of any one of paragraphs 1-61 or 84-87, wherein $R^{20}$ is —H, —$CH_3$, —$CH_2CH_3$, —$CO_2CH_3$, or phenyl.

Paragraph 89. The compound of any one of paragraphs 1-61 or 84-87, wherein $R^{20}$ is —H.

Paragraph 90. The compound of any one of paragraphs 1-61 or 84-89, wherein $R^{21}$ is —H, —$CH_3$, —$CH_2CH_3$, —$CO_2CH_3$, or phenyl.

Paragraph 91. The compound of any one of paragraphs 1-61 or 84-90, wherein $R^{21}$ is —$CH_3$, —$CH_2CH_3$, —$CO_2CH_3$, or phenyl.

Paragraph 92. The compound of any one of paragraphs 1-61 or 84-91, wherein n is 0 and $R^{22}$ and $R^{23}$ are absent.

Paragraph 93. The compound of any one of paragraphs 1-61 or 84-91, wherein n is 1 and $R^{22}$ and $R^{23}$ are —H.

Paragraph 94. The compound of any one of paragraphs 1-61 or 84-93, wherein $R^{24}$ is —H, —CN, —C(O)$CH_3$, —$CO_2CH_3$, —$CH_2CO_2CH_3$, —C(O)N($CH_3$)$_2$, phenyl, cyclopentyl, or cyclohexyl.

Paragraph 95. The compound of any one of paragraphs 1-61 or 84-94, wherein $R^{24}$ is —H, —CN, —C(O)$CH_3$, —$CO_2CH_3$, —$CH_2CO_2CH_3$, —C(O)N($CH_3$)$_2$, phenyl, cyclopentyl, or cyclohexyl.

Paragraph 96. The compound of any one of paragraphs 1-61 or 84-95, wherein $R^{25}$ is —CN, —C(O)$CH_3$, —$CO_2CH_3$, —$CH_2CO_2CH_3$, —C(O)N($CH_3$)$_2$, phenyl, cyclopentyl, or cyclohexyl.

Paragraph 97. The compound of any one of paragraphs 1-61, wherein $R^{27}$ and $R^{28}$ are each independently —H or —Z—$NR^{35}R^{36}$, wherein $R^{35}$ and $R^{36}$ are each independently —H, —$C_1$-$C_6$ alkyl, —$C_1$-$C_6$ alkylene-OH, —$C_1$-$C_6$ alkylene-$NH_2$, —$C_1$-$C_6$ alkylene-NH—$C_1$-$C_6$ alkyl, or —$C_1$-$C_6$ alkylene-N—($C_1$-$C_6$ alkyl)$_2$.

Paragraph 98. The compound of any one of paragraphs 1-61 or 97, wherein $R^{27}$ is —H.

Paragraph 99. The compound of any one of paragraphs 1-61, 97, or 98, wherein $R^{28}$ is —Z—$NR^{35}R^{36}$, wherein Z is $C_1$-$C_4$ alkylene; and $R^{35}$ and $R^{36}$ are each independently —H, —$C_1$-$C_2$ alkyl, —$C_1$-$C_2$ alkylene-OH, —$C_1$-$C_2$ alkylene-$NH_2$, —$C_1$-$C_2$ alkylene-NH—$C_1$-$C_2$ alkyl, or —$C_1$-$C_2$ alkylene-N—($C_1$-$C_2$ alkyl)$_2$.

Paragraph 100. The compound of any one of paragraphs 1-61 or 97-99, wherein $R^{28}$ is —Z—$NR^{35}R^{36}$, wherein $R^{35}$ and $R^{36}$ are each independently —H or —$C_1$-$C_2$ alkyl.

Paragraph 101. The compound of any one of paragraphs 1-61 or 97-100, wherein $R^{28}$ is —CH($CH_3$)$NH_2$, —CH($CH_3$)$CH_2NH_2$, —C($CH_3$)$_2NH_2$, —C($CH_3$)$_2CH_2NH_2$, —$CH_2NH_2$, —N($CH_3$)$_2$, or —N($CH_2CH_3$)$_2$.

Paragraph 102. The compound of any one of paragraphs 1-61 or 97-101, wherein $R^{28}$ is —C($CH_3$)$_2NH_2$.

Paragraph 103. The compound of any one of paragraphs 1-61 or 97-102, wherein p is 0 and $R^{29}$ and $R^{30}$ are absent.

Paragraph 104. The compound of any one of paragraphs 1-61 or 97-103, wherein $R^{31}$ and $R^{32}$ are each independently —H, —C(O)$_2$H, —$CO_2CH_3$, —C(O)N($CH_3$)$_2$, —C(O)N($CH_2CH_3$)$_2$, —$CH_2$C(O)$NH_2$, —$CH_2$C(O)N($CH_3$)$_2$, or —$CH_2$C(O)N($CH_2CH_3$)$_2$.

Paragraph 105. The compound of any one of paragraphs 1-61 or 97-104, wherein $R^{31}$ and $R^{32}$ are each —H.

Paragraph 106. The compound of any one of paragraphs 1-105, wherein the compound has a boiling point above about 225° C.

Paragraph 107. The compound of any one of paragraphs 1-106, wherein the compound has a boiling point of at least about 250° C.

Paragraph 108. The compound of any one of paragraphs 1-107, wherein the compound has a boiling point of at least about 260° C.

Paragraph 109. The compound of any one of paragraphs 1-108, wherein the compound has a boiling point of at least about 270° C.

Paragraph 110. The compound of any one of paragraphs 1-109, wherein the compound has a boiling point of at least about 280° C.

Paragraph 111. The compound of any one of paragraphs 1-110, wherein the compound has a longer gas chromatography retention time than diethyl adipate.

Paragraph 112. The compound of paragraph 111, wherein the retention time is at least about 0.5 second longer than diethyl adipate.

Paragraph 113. The compound of paragraph 111 or paragraph 112, wherein the retention time is at least about 1.0 second longer than diethyl adipate.

Paragraph 114. The compound of any one of paragraphs 1-113, wherein the compound has a longer gas chromatography retention time than hexadecane.

Paragraph 115. The compound of any one of paragraphs 1-114, wherein the retention time is at least about 0.5 second longer than hexadecane.

Paragraph 116. The compound of any one of paragraphs 1-115, wherein the compound has a longer gas chromatography retention time than methyl palmitate.

Paragraph 117. The compound of any one of paragraphs 1-116, wherein the retention time is at least about 0.5 second longer than methyl palmitate.

Paragraph 118. The compound of any one of paragraphs 1-117, wherein the compound is low VOC.

Paragraph 119. The compound of any one of paragraphs 1-118, wherein the compound has a toxicity lower than N-methyl-2-pyrrolidione.

Paragraph 120. A composition comprising the compound of Formula I, Formula II, Formula III, Formula IV, or a combination thereof in any one of paragraphs 1-119.

Paragraph 121. The composition of paragraph 120, wherein the composition is substantially free of N-methyl-2-pyrrolidione (NMP).

Paragraph 122. The composition of paragraph 121, wherein the compound replaces N-methyl-2-pyrrolidione (NMP) in the composition.

Paragraph 123. The composition of any one of paragraphs 120-122, wherein the composition is a paint or coating, stripper (e.g., paint, photoresist, furniture, graffiti, wheel, nail polish remover), cleaner (e.g., oven, surface, floor, automotive, industrial, optic, printed circuit board, or semiconductor), adhesive/binder/sealant, leather treatment, personal care (i.e., commonly used as a surfactant), screen printing (e.g., lithographic, silk), pharmaceutical formulation, and/or manufacturing (e.g., electronic such as printed circuit board, defluxing, or semiconductor; pharmaceutical; agrochemical; petrochemicals; plasticizer; ink).

Paragraph 124. A method of making the compound of Formula I in any one of paragraphs 1-123 comprising: reacting a nitroalkane and an acrylate reagent to form a nitro alkanoyl reagent; optionally derivatizing the nitro alkanoyl reagent; reducing the nitro acrylate reagent to form an amino alkanoyl reagent; optionally derivatizing the amino alkanoyl reagent; cyclizing the amino alkanoyl reagent to form a compound of Formula Ia:

Formula Ia

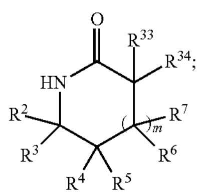

and alkylating the compound of Formula Ia; wherein $R^2$, $R^3$, $R^4$, $R^5$, $R^6$, $R^7$, $R^{33}$, $R^{34}$, and m are as defined in any one of paragraphs 1-123.

Paragraph 125. The method of paragraph 124, wherein the nitroalkane is compound of Formula Ib:

Formula Ib

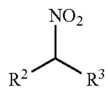

wherein $R^2$ and $R^3$ are as defined in any one of paragraphs 1-123.

Paragraph 126. The method of paragraph 124 or paragraph 125, wherein the acrylate reagent is compound of Formula Ic:

Formula Ic

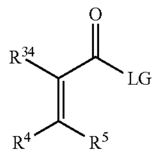

wherein $R^4$, $R^5$, $R^{34}$, and LG are as defined in any one of paragraphs 1-125 and LG is a leaving group.

Paragraph 127. A method of making the compound of Formula I in any one of paragraphs 1-123 comprising: reacting a nitroalkane and a ketone or aldehyde to form a nitroalcohol; optionally derivatizing the nitroalcohol; reducing the nitroalcohol to form an aminoalcohol; optionally derivatizing the aminoalcohol; and cyclizing the aminoalcohol in the presence of carbon dioxide to form a compound of Formula Id:

Formula Id

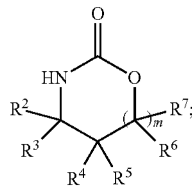

and alkylating the compound of Formula Id; wherein $R^2$, $R^3$, $R^4$, $R^5$, $R^6$, $R^7$, and m are as defined in any one of paragraphs 1-123.

Paragraph 128. The method of paragraph 127, wherein the nitroalkane is compound of Formula Ib:

Formula Ib

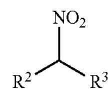

wherein $R^2$ and $R^3$ are as defined in any one of paragraphs 1-123.

Paragraph 129. The method of paragraph 127 or paragraph 128, wherein the ketone or the aldehyde is compound of Formula Ie:

Formula Ie

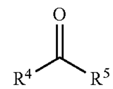

wherein $R^4$ and $R^5$ are as defined in any one of paragraphs 1-123, 127, or 128.

Paragraph 130. A method of making the compound of Formula II in any one of paragraphs 1-123 comprising: reacting a nitroalkane and an acrylate reagent to form a nitro alkanoyl reagent; optionally derivatizing the nitro alkanoyl reagent; reducing the nitro alkanoyl reagent to form a compound of Formula IIa:

Formula IIa

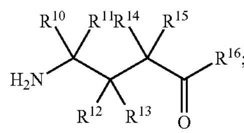

and alkylating the compound of Formula IIa; wherein $R^{10}$, $R^{11}$, $R^{12}$, $R^{13}$, $R^{14}$, $R^{14}$, and $R^{16}$ are as defined in any one of paragraphs 1-123.

Paragraph 131. The method of paragraph 130, wherein the nitroalkane is compound of Formula IIb:

Formula IIb

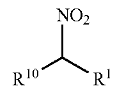

wherein $R^{10}$ and $R^{11}$ are as defined in any one of paragraphs 1-123.

Paragraph 132. The method of paragraph 130 or paragraph 131, wherein the acrylate reagent is compound of Formula IIc:

Formula IIc

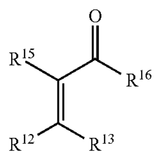

wherein $R^{12}$, $R^{13}$, $R^{1}$, and $R^{16}$ are as defined in any one of paragraphs 1-123.

Paragraph 133. A method of making the compound of Formula III in any one of paragraphs 1-123 comprising: reducing a nitroalkane to form an alkylhydroxylamine; reacting the alkylhydroxylamine and an aldehyde to form a nitrone; and reacting the nitrone and an alkene.

Paragraph 134. The method of paragraph 133, wherein the nitroalkane is a compound of Formula IIIb:

Formula IIIb

wherein $R^{17}$ is defined in any one of paragraphs 1-123.

Paragraph 135. The method of paragraph 133 or paragraph 134, wherein the nitrone is compound of Formula IIIc:

Formula IIIc

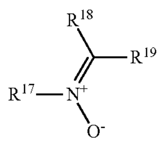

wherein $R^{17}$, $R^{18}$, and $R^{19}$ are as defined in any one of paragraphs 1-123.

Paragraph 136. The method of any one of paragraphs 133-135, wherein the alkene is compound of Formula IIId:

Formula IIId

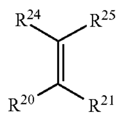

wherein $R^{20}$, $R^{21}$, $R^{24}$, and $R^{25}$ are as defined in any one of paragraphs 1-123.

Paragraph 137. A method of making the compound of Formula IV in any one of paragraphs 1-123 comprising: reacting a nitroalkane and a maleimide to form a nitropyrrolidine-dione; and reducing the nitropyrrolidine-dione to form the compound of Formula IV.

Paragraph 138. The method of paragraph 137, wherein the nitropyrrolidine-dione is compound of Formula IVb:

Formula IVb

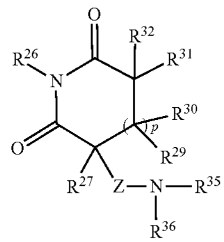

wherein $R^{26}$, $R^{27}$, $R^{29}$, $R^{30}$, $R^{31}$, $R^{32}$, $R^{35}$, $R^{36}$, and Z are defined in any one of paragraphs 1-123.

EQUIVALENTS

While certain embodiments have been illustrated and described, a person with ordinary skill in the art, after reading the foregoing specification, can effect changes, substitutions of equivalents and other types of alterations to the compounds of the present technology or salts, pharmaceutical compositions, derivatives, prodrugs, metabolites, tautomers or racemic mixtures thereof as set forth herein. Each aspect and embodiment described above can also have included or incorporated therewith such variations or aspects as disclosed in regard to any or all of the other aspects and embodiments.

The present technology is also not to be limited in terms of the particular aspects described herein, which are intended as single illustrations of individual aspects of the present technology. Many modifications and variations of this present technology can be made without departing from its spirit and scope, as will be apparent to those skilled in the art. Functionally equivalent methods within the scope of the present technology, in addition to those enumerated herein, will be apparent to those skilled in the art from the foregoing descriptions. Such modifications and variations are intended to fall within the scope of the appended claims. It is to be understood that this present technology is not limited to particular methods, reagents, compounds, compositions, labeled compounds or biological systems, which can, of course, vary. It is also to be understood that the terminology used herein is for the purpose of describing particular aspects only, and is not intended to be limiting. Thus, it is intended that the specification be considered as exemplary only with the breadth, scope and spirit of the present technology indicated only by the appended claims, definitions therein and any equivalents thereof.

The embodiments, illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

In addition, where features or aspects of the disclosure are described in terms of Markush groups, those skilled in the art will recognize that the disclosure is also thereby described in terms of any individual member or subgroup of members of the Markush group. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member.

All publications, patent applications, issued patents, and other documents (for example, journals, articles and/or textbooks) referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

Other embodiments are set forth in the following claims, along with the full scope of equivalents to which such claims are entitled.

What is claimed is:

1. A composition comprising (a) a compound of Formula I:

Formula I

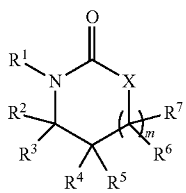

wherein:

X is O or $CR^{33}R^{34}$;

$R^1$ is $—CH_3$, $—CH_2CH_3$, $—CH_2CH_2CH_3$, or $—CH(CH_3)_2$;

$R^2$ and $R^3$ are each independently —H, $—CH_3$, or $—CH_2CH_3$;

$R^6$ and $R^7$ are each independently absent, —H, $—CH_3$, $—CH_2CH_3$, —CN, $—C(O)N(CH_3)_2$, $—CH_2C(O)N(CH_3)_2$, $—C(O)N(CH_2CH_3)_2$, $—CH_2C(O)N(CH_2CH_3)_2$, $—CO_2CH_3$, or $—CH_2CO_2CH_3$;

$R^4$, $R^5$, $R^{33}$, and $R^{34}$ are each independently —H, —CN, $—C_1$-$C_8$ alkyl, $—C_2$-$C_8$ (hetero)cycloalkyl, $—O—C_1$-$C_8$ alkyl, $—CH_2—O—C_1$-$C_8$ alkyl, $—C(O)—C_1$-$C_8$ alkyl, $—C_1$-$C_8$ alkylene-C(O)—$C_1$-$C_8$ alkyl, $—C(O)—C_3$-$C_8$cycloalkyl, $—C_1$-$C_8$ alkylene-C(O)—$C_2$-$C_8$ (hetero)cycloalkyl, $—CO_2H$, $—CO_2$-$C_1$-$C_8$ alkyl, $—C_1$-$C_8$ alkylene-$CO_2—C_1$-$C_8$ alkyl, $—CO_2—C_2$-$C_8$ (hetero)cycloalkyl, $—C_1$-$C_8$ alkylene-$CO_2$-$C_2$-$C_8$ (hetero)cycloalkyl, $—NH_2$, $—C_1$-$C_8$ alkylene-$NH_2$, $—NH—C_1$-$C_8$ alkyl, $—N(C_1$-$C_8$ alkyl$)_2$, $—C_1$-$C_8$ alkylene-NH—$C_1$-$C_8$ alkyl, $—C_1$-$C_8$ alkylene-N($C_1$-$C_8$ alkyl$)_2$, $—C(O)NH_2$, $—C_1$-$C_8$ alkylene-C(O)$NH_2$, —C(O)NH—$C_1$-$C_8$ alkyl, —C(O)N($C_1$-$C_8$ alkyl$)_2$, $—C_1$-$C_8$ alkylene-C(O)NH—$C_1$-$C_8$ alkyl, $—C_1$-$C_8$ alkylene-C(O)N($C_1$-$C_8$ alkyl$)_2$, -(hetero)aryl, -(hetero)cycloalkyl,

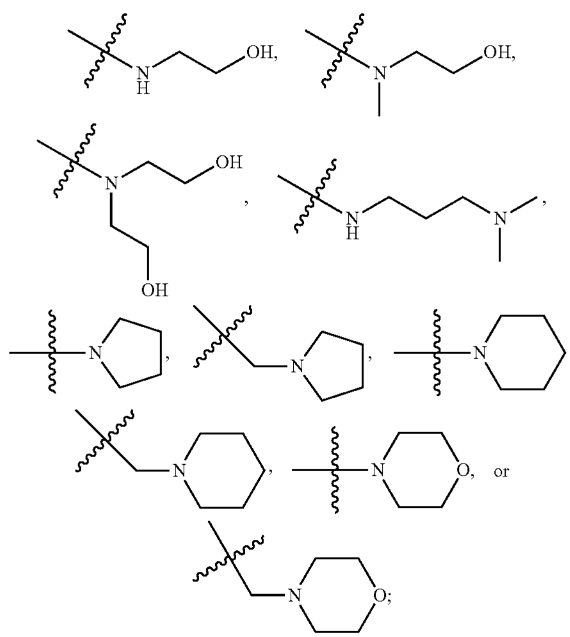

and m is 0 or 1; provided that when X is $CR^{33}R^{34}$, then m is 0, $R^6$ and $R^7$ are both absent, and $R^2$ and $R^3$ are both not H;

(b) water, $C_1$-$C_6$ alcohol, ethylene glycol monophenyl ether, methoxy polyethylene glycol, tripropylene glycol methyl ether, diethylene glycol monophenyl ether, diethylene glycol monobutyl ether, phenylglycol ethers, ethanol, tetrahydrofuran, methyl ethyl ketone, methylacetate, naphtha, turpentine, dichloropropane, toluene, xylene, or a combination of any two or more thereof; and (c) one or more components selected from binders, pigments, dyes, dispersants, bases, surfactants, thickeners, humectants, alkali metal carbonate salts, alkali metal bicarbonate salts, metal chelating agent, ammonium fluoride, resins, polymers, fillers, thixotropic agents, plasticizers, lime, cement, gypsum, liquid glass, carbohydrates, wax, linseed oil, gum arabic, gums, casein, oil, alpha-hydroxy acids, polyhydroxy acids, hydroquinone, retinol, kojic acid, copper peptide, vitamins, minerals, moisturizers, emollients, humectants, lubricating agents, sensates, fragrances, anti-dandruff agents, buffering agents, bulking agents, chelating agents, colorants, astringents, cosmetic biocides, denaturants, anti-inflammatory agents, sunscreen agents, film formers, pH adjusters, propellants, reducing agents, sequestrants, conditioning agents, detersive agents, or a combination of two or more thereof.

2. The composition of claim 1, wherein $R^6$ and $R^7$ are each absent and m is 0.

3. The composition of claim 1, wherein $R^6$ is —H, —$CH_3$, —$CH_2CH_3$, —CN, —$C(O)N(CH_3)_2$, —$CH_2C(O)N(CH_3)_2$, —$CO_2CH_3$, or —$CH_2CO_2CH_3$.

4. The composition of claim 1, wherein $R^7$ is —H, —$CH_3$, —$CH_2CH_3$ —CN, —$C(O)N(CH_3)_2$, —$CH_2C(O)N(CH_3)_2$, —$CO_2CH_3$, or $CH_2CO_2CH_3$.

5. The composition of claim 1, wherein $R^4$, $R^5$, $R^{33}$, and $R^{34}$ are each independently —H, —CN, —$CH_3$, —$CH_2CH_3$, —$OCH_3$, —$OCH_2CH_3$, —$C(O)CH_3$, —$C(O)CH_2CH_3$, —$CH_2C(O)CH_3$, —$CH_2COCH_2CH_3$, —$C(O)_2H$, —$CO_2CH_3$, —$CO_2CH_2CH_3$, —$CH_2CO_2CH_3$, —$CH_2CO_2CH_2CH_3$, —$NH_2$, —$CH(CH_3)NH_2$, —$CH_2CH(CH_3)NH_2$, —$CH(CH_3)CH_2NH_2$, —$C(CH_3)_2NH_2$, —$CH_2C(CH_3)_2NH_2$, —$C(CH_3)_2CH_2NH_2$, —$CH_2NH_2$, —$CH_2CH_2NH_2$, —$CH_2CH_2CH_2NH_2$, —$N(CH_3)_2$, —$N(CH_2CH_3)_2$, —$CH_2N(CH_3)_2$, —$CH_2N(CH_2CH_3)_2$, —$C(O)N(CH_3)_2$, —$C(O)N(CH_2CH_3)_2$, —$CH_2C(O)NH_2$, —$CH_2C(O)N(CH_3)_2$, —$CH_2C(O)N(CH_2CH_3)_2$, $C_4$-$C_{12}$ (hetero)aryl, $C_2$-$C_8$ (hetero)cycloalkyl,

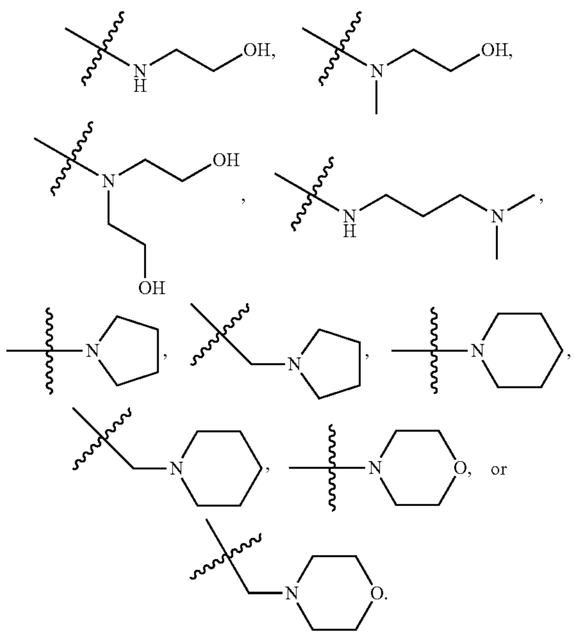

6. The composition of claim 1, wherein $R^4$, $R^5$, $R^{33}$, and $R^{34}$ are each independently —H, —CN, —$CH_3$, —$CH_2CH_3$, —$C(O)CH_3$, —$C(O)CH_2CH_3$, —$CH_2C(O)CH_3$, —$CH_2COCH_2CH_3$, —$CO_2H$, —$CO_2CH_3$, —$CO_2CH_2CH_3$, —$CH_2CO_2CH_3$, —$CH_2CO_2CH_2CH_3$, —$C(O)N(CH_3)_2$, —$C(O)N(CH_2CH_3)_2$, —$CH_2C(O)NH_2$, —$CH_2C(O)N(CH_3)_2$, —$CH_2C(O)N(CH_2CH_3)_2$,

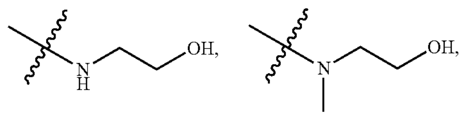

-continued

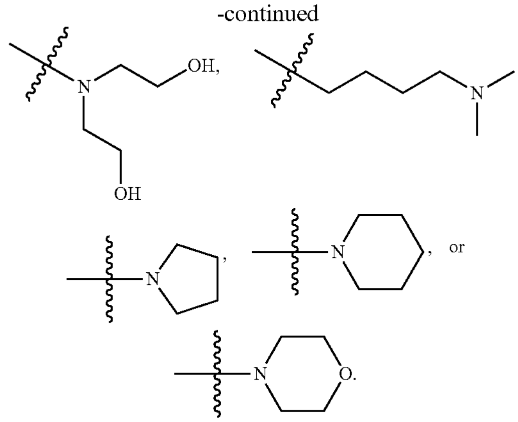

7. The composition of claim 1, wherein $R^4$, $R^5$, $R^{33}$, and $R^{34}$ are each independently —H, —CN, —$CH_3$, —$CH_2CH_3$, —$C(O)CH_3$, —$CH_2C(O)CH_3$, —$CO_2H$, —$CO_2CH_3$, —$CH_2CO_2CH_3$, or —$C(O)N(CH_3)_2$.

8. The composition of claim 1, wherein X is $CR^{33}R^{34}$ and at least one of $R^4$, $R^5$, $R^{33}$, and $R^{34}$ is not H; or wherein X is O.

9. The composition of claim 8, wherein $R^4$ is —H and at least one of $R^5$, $R^{33}$, and $R^{34}$ is not —H or $R^4$, $R^5$, $R^{33}$, and $R^{34}$ are each —H and at least one of $R^6$ and $R^7$ is not —H.

10. The composition of claim 1, wherein the compound has one or more of:

(a) a boiling point above about 225° C.;

(b) a longer gas chromatography retention time than diethyl adipate, hexadecane, methyl palmitate, or a combination of two or more thereof; and (c) a toxicity lower than N-methyl-2-pyrrolidone as determined by dermal LD50 in rats.

11. The composition of claim 1, wherein the composition is substantially free of N-methyl-2-pyrrolidone (NMP) or wherein the composition is a known composition to contain NMP and the compound replaces the NMP in the composition.

12. A method of making the compound of Formula I in claim 1 comprising:

reacting a nitroalkane and an acrylate reagent to form a nitro alkanoyl reagent;

optionally derivatizing the nitro alkanoyl reagent;

reducing the nitro acrylate reagent to form an amino alkanoyl reagent;

optionally derivatizing the amino alkanoyl reagent;

cyclizing the amino alkanoyl reagent to form a compound of Formula Ia:

Formula Ia

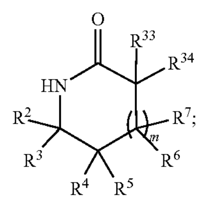

and alkylating the compound of Formula Ia;

wherein $R^2$, $R^3$, $R^4$, $R^5$, $R^6$, $R^7$, $R^{33}$, $R^{34}$, and m are as defined in claim 1.

13. A method of making the compound of Formula I in claim 1 comprising:

reacting a nitroalkane and a ketone or aldehyde to form a nitroalcohol;

optionally derivatizing the nitroalcohol;

reducing the nitroalcohol to form an aminoalcohol;

optionally derivatizing the aminoalcohol; and cyclizing the aminoalcohol in the presence of carbon dioxide to form a compound of Formula Id:

Formula Id

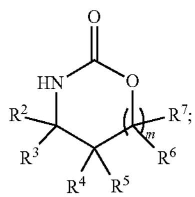

and alkylating the compound of Formula Id;

wherein $R^2$, $R^3$, $R^4$, $R^5$, $R^6$, $R^7$, and m are as defined in claim 1.

14. The composition of claim 1, wherein the compound of Formula (I) is:

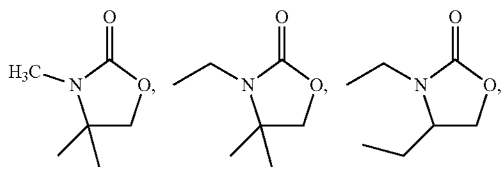

-continued

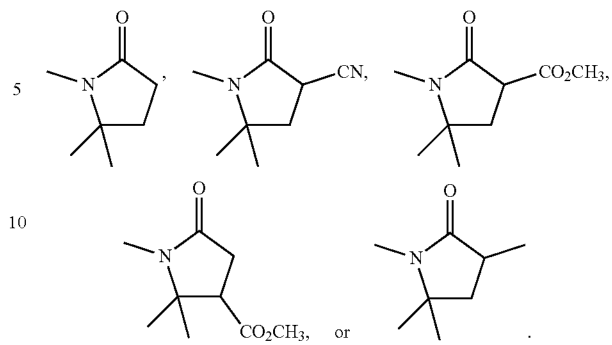

15. The composition of claim 1, wherein the composition is a paint, coating, stripper, cleaner, adhesive, binder, sealant, leather treatment formulation, personal care formulation, screen printing formulation, pharmaceutical formulation, or a manufacturing formulation.

16. The composition claim 1, wherein the composition is a stripper for paint, photoresist, furniture, graffiti, wheel, and nail polish remover.

17. The composition claim 1, wherein the composition is a cleaner for an oven, surface, floor, automotive, industrial, optic, printed circuit board, or semiconductor.

18. The composition claim 1, wherein the composition comprises (c) one or more components selected from surfactants, thickeners, metal chelating agent, ammonium fluoride, buffering agents, chelating agents, or a combination of two or more thereof.

* * * * *